US012691119B2

(12) United States Patent
Clark et al.

(10) Patent No.: US 12,691,119 B2
(45) Date of Patent: Jul. 28, 2026

(54) METHODS FOR TREATING COVID-19 WITH SEPIAPTERIN

(71) Applicants: PTC Therapeutics MP, Inc., South Plainfield, NJ (US); Virginia Commonwealth University, Richmond, VA (US)

(72) Inventors: Gene Chatman Clark, Richmond, VA (US); Eleonora Mezzaroma, Glen Allen, VA (US); Christopher Rabender, Chesterfield, VA (US); Ross B. Mikkelsen, Richmond, VA (US); Vasily Yakovlev, Richmond, VA (US); Neil Smith, Cary, NC (US)

(73) Assignees: PTC Therapeutics MP, Inc., Warren, NJ (US); Virginia Commonwealth University, Richmond, VA (US)

( * ) Notice: Subject to any disclaimer, the term of this patent is extended or adjusted under 35 U.S.C. 154(b) by 418 days.

(21) Appl. No.: 18/276,594

(22) PCT Filed: Feb. 9, 2022

(86) PCT No.: PCT/US2022/015810
§ 371 (c)(1),
(2) Date: Aug. 9, 2023

(87) PCT Pub. No.: WO2022/173823
PCT Pub. Date: Aug. 18, 2022

(65) Prior Publication Data
US 2024/0122931 A1      Apr. 18, 2024

Related U.S. Application Data

(60) Provisional application No. 63/147,688, filed on Feb. 9, 2021.

(51) Int. Cl.
*A61K 31/519*          (2006.01)
(52) U.S. Cl.
CPC ................................. *A61K 31/519* (2013.01)
(58) Field of Classification Search
CPC .................................................. A61K 31/519
See application file for complete search history.

(56) References Cited

U.S. PATENT DOCUMENTS

| | | |
|---|---|---|
| 9,181,254 B2 | 11/2015 | Yoshino et al. |
| 11,072,614 B2 | 7/2021 | Levy |
| 11,130,760 B2 | 9/2021 | Yoshino et al. |
| 11,173,158 B2 | 11/2021 | Hasegawa et al. |
| 11,617,752 B2 | 4/2023 | Smith et al. |
| 11,752,154 B2 | 9/2023 | Levy |
| 11,773,097 B2 | 10/2023 | Levy |
| 2011/0098306 A1* | 4/2011 | Pasricha |
| 2021/0161901 A1 | 6/2021 | Smith et al. |
| 2021/0269443 A1 | 9/2021 | Levy et al. |
| 2022/0081443 A1 | 3/2022 | Yoshino et al. |
| 2022/0273661 A1 | 9/2022 | Mezzaroma et al. |
| 2022/0362249 A1 | 11/2022 | Smith |
| 2023/0110351 A1 | 4/2023 | Smith |
| 2023/0381181 A1 | 11/2023 | Smith et al. |
| 2024/0043426 A1 | 2/2024 | Levy |
| 2024/0100054 A1 | 3/2024 | Levy |
| 2024/0115572 A1 | 4/2024 | Rabender et al. |

FOREIGN PATENT DOCUMENTS

| | | |
|---|---|---|
| WO | WO-2019/175328 A1 | 9/2019 |
| WO | WO-2019/232130 A1 | 12/2019 |
| WO | WO-2023/055923 A1 | 4/2023 |

OTHER PUBLICATIONS

Wahl, et al., SARS-CoV-2 infection is effectively treated and prevented by EIDD-2801, Nature 591, pp. 451-457 (2021) is relevant prior art regarding pharmaceutical treatment of SARS-COV-2. (Year: 2021).*
Smith et al., "Phase I clinical evaluation of CNSA-001 (sepiapterin), a novel pharmacological treatment for phenylketonuria and tetrahydrobiopterin deficiencies, in healthy volunteers," Mol Genet Metab.126(4):406-12 (Feb. 2019) (7 pages).

* cited by examiner

*Primary Examiner* — Erich A Leeser
(74) *Attorney, Agent, or Firm* — Clark & Elbing LLP

(57) ABSTRACT

The invention features methods of treating a SARS-CoV-2 infection in a subject, the method comprising administering to the subject an effective amount of sepiapterin or a pharmaceutically acceptable salt thereof.

17 Claims, 4 Drawing Sheets

METHODS FOR TREATING COVID-19 WITH SEPIAPTERIN

CROSS-REFERENCE TO RELATED APPLICATIONS

This application claims the benefit of, and priority to U.S. Provisional Patent Application Ser. No. 63/147,688, filed Feb. 9, 2021, the contents of which are expressly incorporated by reference to the present application in its entirety.

BACKGROUND OF THE INVENTION

The majority of patients infected with SARS-CoV-2, which causes the disease COVID-19, clear the infection without treatment or the need for hospitalization. However, in about 15% of symptomatic patients, the virus is not effectively cleared, leading to progression to the severe phase of the disease. (1) This phase is characterized by acute respiratory distress, often with lymphocytopenia in the presence of high WBC, and a high viral load in the intestine, kidney, and lungs. (2) It is unclear what may predispose some patients to disease progression. However, it has been speculated that, given the low T cell count and high viral load observed in these patients, that this is the result of a failure to quickly develop an effective adaptive immune response to the virus. The use of immune stimulating interventions such as pegylated interferon has been suggested to decrease the risk of disease progression. (3) However, this approach may be limited as global immune activators may themselves carry the risk of exacerbating the severity of acute respiratory distress.

Sepiapterin, a metabolic precursor of the enzyme cofactor BH4, with good oral bioavailability and an excellent safety profile in humans, is currently being tested for the treatment for certain metabolic disorders.

What is needed are methods for treating SARS-CoV2 infection. What is further needed are methods of treating SARS-CoV2 infection without enhancing the risk of severe immune related events. What is further needed are methods of preventing or mitigating acute respiratory distress.

SUMMARY OF THE INVENTION

Provided are methods of treating a SARS-CoV-2 infection in a subject, comprising administering to the subject an effective amount of sepiapterin or a pharmaceutically acceptable salt thereof. In some embodiments, the infection is a symptomatic infection. In some embodiments, the infection is an asymptomatic infection. In some embodiments, including any of the foregoing embodiments, the sepiapterin is administered as soon as the subject demonstrates one or more symptoms of the disease. In some embodiments, including any of the foregoing embodiments, the method comprises preventing, delaying, or mitigating acute respiratory distress. In some embodiments, including any of the foregoing embodiments, the subject has acute respiratory distress. In some embodiments, including any of the foregoing embodiments, the method comprises preventing, delaying, or mitigating sepsis in the subject. In some embodiments, including any of the foregoing embodiments, the effective amount of sepiapterin, or pharmaceutically acceptable salt thereof, is about 10 mg/kg to about 60 mg/kg per dose. In some embodiments, including any of the foregoing embodiments, the effective amount of sepiapterin, or pharmaceutically acceptable salt thereof, is about 20 mg/kg to about 60 mg/kg per dose. In some embodiments, including any of the foregoing embodiments, the effective amount of sepiapterin, or pharmaceutically acceptable salt thereof, is about 10 mg/kg per dose. In some embodiments, including any of the foregoing embodiments, the effective amount of sepiapterin, or pharmaceutically acceptable salt thereof, is about 20 mg/kg per dose. In some embodiments, including any of the foregoing embodiments, the effective amount of sepiapterin, or pharmaceutically acceptable salt thereof, is about 40 mg/kg per dose. In some embodiments, including any of the foregoing embodiments, the effective amount of sepiapterin, or pharmaceutically acceptable salt thereof, is about 60 mg/kg per dose. In some embodiments, including any of the foregoing embodiments, the effective amount of sepiapterin, or pharmaceutically acceptable salt thereof, is administered once daily. In some embodiments, including any of the foregoing embodiments, the effective amount of sepiapterin, or pharmaceutically acceptable salt thereof, is administered twice daily. In some embodiments, including any of the foregoing embodiments, the effective amount of sepiapterin, or pharmaceutically acceptable salt thereof, is administered in two equal doses. In some embodiments, including any of the foregoing embodiments, the effective amount of sepiapterin, or a pharmaceutically acceptable salt thereof, is administered with food. In some embodiments, including any of the foregoing embodiments, administration to the subject occurs less than 30 minutes prior to consuming food or after consuming food. In some embodiments, including any of the foregoing embodiments, the administration to the subject is substantially at the same time as food. In some embodiments, including any of the foregoing embodiments, the food is high protein and/or high fat food. In some embodiments, including any of the foregoing embodiments, the food is a low fat food. In some embodiments, including any of the foregoing embodiments, the food is high calorie food. In some embodiments, including any of the foregoing embodiments, the effective amount of sepiapterin, or a pharmaceutically acceptable salt thereof, is administered without food. In some embodiments, including any of the foregoing embodiments, administration to the subject occurs more than 30 minutes before, or more than 30 minutes after consuming food. In some embodiments, including any of the foregoing embodiments, administration to the subject occurs more than 30 minutes before, or more than 2 hours after consuming food. In some embodiments, including any of the foregoing embodiments, administration to the subject occurs more than 30 minutes before, or more than 3 hours after consuming food. In some embodiments, including any of the foregoing embodiments, the sepiapterin or a pharmaceutically acceptable salt thereof, is formulated as an oral powder for suspension. In some embodiments, including any of the foregoing embodiments, the sepiapterin or a pharmaceutically acceptable salt thereof, is administered as a suspension in a flavored suspending vehicle. In some embodiments, including any of the foregoing embodiments, the sepiapterin or a pharmaceutically acceptable salt thereof, is administered as a suspension in water or juice (e.g., apple, orange, grape, etc.). In some embodiments, including any of the foregoing embodiments, the sepiapterin or a pharmaceutically acceptable salt thereof, is formulated as an oral tablet, capsule, or caplet.

In some embodiments of any of the methods described herein, administering sepiapterin, or a pharmaceutically acceptable salt thereof, produces a BH4 concentration of at least 50 ng/mL (e.g., at least 60 ng/mL, at least 100 ng/mL, at least 200 ng/mL, at least 400 ng/mL, at least 600 ng/mL, at least 1000 ng/mL, or at least 2000 ng/mL or from 50 ng/mL to 100 ng/mL from 60 ng/mL to 400 ng/mL, from 200 ng/mL to 600 ng/mL, from 400 ng/mL to 1000 ng/mL, or from 600 ng/mL to 1500 ng/mL) in the plasma of the subject within 10 hours of administration.

In some embodiments of any of the methods described herein, the effective amount is an amount (e.g., 2.5 mg/kg to 100 mg/kg per dose) sufficient to produce a BH4 concentration of at least 50 ng/mL (e.g., at least 60 ng/mL, at least 100 ng/mL, at least 200 ng/mL, at least 400 ng/mL, at least 600 ng/mL, at least 1000 ng/mL, or at least 2000 ng/mL, or from 50 ng/mL to 100 ng/mL from 60 ng/mL to 400 ng/mL, from 200 ng/mL to 600 ng/mL, from 400 ng/mL to 1000 ng/mL, or from 600 ng/mL to 1500 ng/mL) in the plasma of the subject within 10 hours of administration of the sepiapterin or a pharmaceutically acceptable salt thereof.

In some embodiments of any of the methods described herein, the effective amount of sepiapterin, or a pharmaceutically acceptable salt thereof, is about 1 mg/kg to 100 mg/kg per dose, or about 2.5 mg/kg to 100 mg/kg per dose (e.g., about 20 mg/kg to about 60 mg/kg, or about 20 mg/kg, about 30 mg/kg, about 40 mg/kg, about 50 mg/kg, about 60 mg/kg).

In some embodiments of any of the methods described herein, the effective amount of sepiapterin, or a pharmaceutically acceptable salt thereof, is administered with food. In some embodiments of any of the methods described herein, the effective amount is an amount (e.g., 1 mg/kg to 100 mg/kg per dose, or about 2.5 mg/kg to 100 mg/kg per dose) sufficient to produce a BH4 concentration of at least 50 ng/mL (e.g., at least 60 ng/mL, at least 100 ng/mL, at least 200 ng/mL, at least 400 ng/mL, at least 600 ng/mL, at least 1000 ng/mL, or at least 2000 ng/mL, or from 50 ng/mL to 100 ng/mL from 60 ng/mL to 400 ng/mL, from 200 ng/mL to 600 ng/mL, from 400 ng/mL to 1000 ng/mL, or from 600 ng/mL to 1500 ng/mL) in the plasma of the subject within 10 hours of administration with food. In some embodiments, the effective amount includes a dose that is at least 5% (at least 10%, at least 20%, at least 50%, at least 70%, at least 90%, at least 100%, at least 110%, at least 120%, at least 130%, at least 140%, or at least 150%) lower than the dose sufficient to produce a maximum BH4 plasma concentration (Cmax) of at least 50 ng/mL (e.g., at least 60 ng/mL, at least 100 ng/mL, at least 200 ng/mL, at least 400 ng/mL, at least 600 ng/mL, at least 1000 ng/mL, or at least 2000 ng/mL, or from 50 ng/mL to 100 ng/mL from 60 ng/mL to 400 ng/mL, from 200 ng/mL to 600 ng/mL, from 400 ng/mL to 1000 ng/mL, or from 600 ng/mL to 1500 ng/mL) in the plasma of the subject within 10 hours of administration of sepiapterin, or a pharmaceutically acceptable salt thereof, without food.

In some embodiments of any of the methods described herein, administration to the subject occurs less than 30 minutes prior to consuming food, or after consuming food, e.g., immediately prior to the consumption of food or up to 1 hour after consumption. In some embodiments, the administration to the subject is substantially at the same time as food. In some embodiments of any of the methods described herein, the food is a high protein food. In some embodiments of any of the methods described herein, the food is a high fat food (e.g., at least 25, 30, 40, or 50% of the calories are from fat). In some embodiments of any of the methods described herein, the food is a high protein and high fat food. In some embodiments, the food is high calorie food (e.g., the food includes at least 100 calories, e.g., at least 200 calories, at least 300 calories, at least 400 calories, at least 500 calories, e.g., 500-1500 or 800-1000 calories). In some embodiments of any of the methods described herein, the food is a meal, e.g., breakfast, lunch, or dinner. In some embodiments of any of the methods described herein, the food is a low fat food (e.g. no more than 25% of the calories are from fat).

In some embodiments of any of the methods described herein, the administration with food (e.g., occurring less than 30 minutes prior to consuming food, or after consuming food, e.g., immediately prior to the consumption of food up to 1 hour after consumption) results in an increase (e.g., at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, or at least 150%) in the Cmax of BH4 compared to administration without food (e.g., occurring more than 2 hours after consuming food until 30 minutes prior to consuming further food).

In some embodiments of any of the methods described herein, the administration with food (e.g., occurring less than 30 minutes prior to consuming food or after consuming food, e.g., immediately prior to the consumption of food up to 1 hour after consumption) results in an increase (e.g., at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, or at least 150%) in the extent of production and resulting plasma exposure ($AUC_{0-last}$) of BH4 compared to administration without food (e.g., occurring less than 30 minutes prior to consuming food or after consuming food, e.g., immediately prior to the consumption of food up to 1 hour after consumption).

In some embodiments of any of the methods described herein, the sepiapterin, or a pharmaceutically acceptable salt thereof, is provided in a separate composition from the consumed food (e.g., the sepiapterin, or a pharmaceutically acceptable salt thereof, is not incorporated into a food product). In some embodiments of any of the methods described herein, the consumption of food occurs prior to the administration of sepiapterin or a pharmaceutically acceptable salt thereof (e.g., the consumption of food occurs between 1 hour up to immediately prior to the administration of sepiapterin or a pharmaceutically acceptable salt thereof). In some embodiments of any of the methods described herein, the consumption of food occurs after the administration of sepiapterin or a pharmaceutically acceptable salt thereof (e.g., the consumption of food occurs between immediately after administration up to 30 minutes after administration).

In some embodiments of any of the foregoing methods, the effective amount is an amount (e.g., 2.5 mg/kg to 100 mg/kg per dose) sufficient to produce a sepiapterin plasma concentration of at least 0.5 ng/mL (e.g., at least 1 ng/mL, at least 1.5 ng/mL, at least 2.5 ng/mL, or at least 3.5 ng/mL) in the plasma of the subject within 1 hour of administration without food, e.g., the effective amount includes a dose that is at least 10% (e.g., at least 20%, at least 40%, at least 60%, at least 80%, at least 100%, or at least 120%) lower than the dose sufficient to produce a maximum plasma concentration (Cmax) of at least 0.5 ng/mL (e.g., at least 1 ng/mL, at least 1.5 ng/mL, at least 2.5 ng/mL, or at least 3.5 ng/mL) in the plasma of the subject within 1 hour of administration of sepiapterin with food. In some embodiments, the administration (e.g., occurring more than about 30 minutes prior to or at least 2 hours after consuming food) results in an increase (e.g., at least 10% (at least 20%, at least 40%, at least 60%, at least 80%, at least 100%, or at least 120%) in the maximum plasma, CSF, and/or brain concentration (Cmax) of sepiapterin compared to administration with food (e.g., occurring less than 30 minutes prior to 2 hours after consuming food). In some embodiments, the administration (e.g., occurring more than 30 minutes prior or at least 2 hours after consuming food) results in an increase (e.g., at least 10% (at least 20%, at least 40%, at least 60%, at least 80%, at least 100%, or at least 120%) in the extent of absorption ($AUC_{0\text{-}last}$) of sepiapterin compared to administration with food (e.g., the administration to the subject occurs less than 30 minutes prior to less than 2 hours after consuming food).

In some embodiments of any of the methods described herein, the effective amount of sepiapterin, or a pharmaceutically acceptable salt thereof, is administered in two equal doses (e.g., two doses at different times of day). In some embodiments of any of the methods described herein, the effective amount of sepiapterin, or a pharmaceutically acceptable salt thereof, is administered once per day. In some embodiments of any of the methods described herein, the effective amount of sepiapterin, or a pharmaceutically acceptable salt thereof, is administered in two 60 mg/kg doses (e.g., one 60 mg/kg dose in the morning and one 60 mg/kg dose in the evening). In some embodiments of any of the methods described herein, the effective amount of sepiapterin, or a pharmaceutically acceptable salt thereof, is administered in two 40 mg/kg doses (e.g., one 40 mg/kg dose in the morning and one 40 mg/kg dose in the evening). In some embodiments of any of the methods described herein, the effective amount of sepiapterin, or a pharmaceutically acceptable salt thereof, is administered in two 30 mg/kg doses (e.g., one 30 mg/kg dose in the morning and one 30 mg/kg dose in the evening). In some embodiments of any of the methods described herein, the effective amount of sepiapterin, or a pharmaceutically acceptable salt thereof, is administered in two 20 mg/kg doses (e.g., one 20 mg/kg dose in the morning and one 20 mg/kg dose in the evening). In some embodiments of any of the methods described herein, the effective amount of sepiapterin, or a pharmaceutically acceptable salt thereof, is administered in two 10 mg/kg doses (e.g., one 10 mg/kg dose in the morning and one 10 mg/kg dose in the evening).

In embodiments of any of the methods described herein, the method includes administering to the subject an effective amount of sepiapterin, or a pharmaceutically acceptable salt thereof, with food once per day. In embodiments of any of the methods described herein, the method includes administering to the subject an effective amount of sepiapterin, or a pharmaceutically acceptable salt thereof, with food more than once per day, e.g., twice per day. In embodiments of any of the methods described herein, the method includes administering to the subject an effective amount of sepiapterin, or a pharmaceutically acceptable salt thereof, without food once per day. In embodiments of any of the methods described herein, the method includes administering to the subject an effective amount of sepiapterin, or a pharmaceutically acceptable salt thereof, without food more than once per day, e.g., twice per day.

In some embodiments of any of the methods described herein, the subject is a child (e.g. the subject is less than 18 years old, less than 17 years old, less than 16 years old, less than 15 years old, less than 14 years old, less than 13 years old, less than 12 years old, less than 11 years old, less than 10 years old, less than 9 years old, less than 8 years old, less than 7 years old, less than 6 years old, less than 5 years old, less than 4 years old, less than 3 years old, less than 2 years old, less than 1 year old). In some embodiments of any of the methods described herein, the subject is an adult (e.g., the subject is greater than 18 years old). In some embodiments, the subject is greater than 20 years old, greater than 30 years old, greater than 40 years old, greater than 50 years old, greater than 60 years old, greater than 7 years old, greater than 80 years old, greater than 90 years old.

In some embodiments of any of the methods described herein, the sepiapterin or pharmaceutically acceptable salt thereof is formulated as an oral powder for suspension. In some embodiments of any of the methods described herein, the sepiapterin or a pharmaceutically acceptable salt thereof, is administered as a suspension in a flavored suspending vehicle (e.g., MEDISCA®Oral Mix). In some embodiments of any of the methods described herein, the sepiapterin or a pharmaceutically acceptable salt thereof, is administered as a suspension in water or juice (e.g., apple juice). In some embodiments of any of the methods described herein, the sepiapterin or a pharmaceutically acceptable salt thereof, is administered as a suspension a food such as apple sauce or pudding. In some embodiments of any of the methods described herein, the sepiapterin or pharmaceutically acceptable salt thereof is formulated as a tablet, capsule, or caplet.

In some embodiments of any of the methods described herein, the administration of sepiapterin or pharmaceutically acceptable salt thereof is initiated upon the subject receiving a positive test for SARS-CoV-2 infection. In some embodiments of any of the methods described herein, the administration of sepiapterin or pharmaceutically acceptable salt thereof is initiated prior to the subject receiving a positive test for SARS-CoV-2 infection, for example, in a subject who has been exposed to SARS-CoV-2. In some embodiments of any of the methods described herein, the administration of sepiapterin or pharmaceutically acceptable salt thereof is initiated prior to the subject displaying any symptoms of the infection. In some embodiments of any of the methods described herein, the administration of sepiapterin or pharmaceutically acceptable salt thereof is initiated upon the subject displaying one or more symptoms of the infection. In some embodiments of any of the methods described herein, the subject is administered sepiapterin for at least about 7 days, at least about 14 days (e.g., 14-30 days), at least about 21 days, at least about 28 days, at least about 60 days, at least about 90 days. In some embodiments of any of the methods described herein, the subject is administered sepiapterin as long as the subject displays any symptoms of the infection. In some embodiments of any of the methods described herein, the method comprises preventing, delaying, or mitigating acute respiratory distress. In some embodiments of any of the methods described herein, the method comprises preventing, delaying, or mitigating fibrotic disease resulting from acute respiratory distress. In some embodiments of any of the methods described herein, the subject has acute respiratory distress. In some embodiments of any of the methods described herein, the method comprises preventing, delaying, or mitigating sepsis in the subject.

Definitions

In this application, unless otherwise clear from context, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the term "approximately" may be understood to permit standard variation as would be understood by those of ordinary skill in the art; and (v) where ranges are provided, endpoints are included.

It is to be understood that the description of compounds, compositions, formulations, and methods of treatment described herein include "comprising", "consisting of", and "consisting essentially of" embodiments. In some embodiments, for all compositions described herein, and all methods using a composition described herein, the compositions can either comprise the listed components or steps, or can "consist essentially of" the listed components or steps. When a composition is described as "consisting essentially of" the listed components, the composition contains the components listed, and may contain other components which do not substantially affect the condition being treated, but do not contain any other components which substantially affect the condition being treated other than those components expressly listed; or, if the composition does contain extra components other than those listed which substantially affect the condition being treated, the composition does not contain a sufficient concentration or amount of the extra components to substantially affect the condition being treated. When a method is described as "consisting essentially of" the listed steps, the method contains the steps listed, and may contain other steps that do not substantially affect the condition being treated, but the method does not contain any other steps which substantially affect the condition being treated other than those steps expressly listed. As a non-limiting specific example, when a composition is described as 'consisting essentially of' a component, the composition may additionally contain any amount of pharmaceutically acceptable carriers, vehicles, or diluents and other such components which do not substantially affect the condition being treated.

Unless otherwise clear from context, all references to sepiapterin contained herein refer to sepiapterin or a pharmaceutically acceptable salt of sepiapterin.

As used herein, the term "about" represents a value that is in the range of ±10% of the value that follows the term "about." Reference to "about" a value or parameter herein includes (and describes) variations that are directed to that value or parameter per se. For example, description referring to "about X" includes description of "X".

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal, and vitreal.

A "symptomatic infection" indicates the subject infected with SARS-CoV2 has one or more symptoms of SARS-CoV-2 infection including, but not limited to: fever, chills, cough, shortness of breath or difficulty breathing, fatigue, muscle or body aches, headache, loss of taste or smell, sore throat, congestion or runny nose, nausea, vomiting, or diarrhea.

An "asymptomatic infection" indicates the subject infected with SARS-CoV2 has not developed any symptoms of SARS-CoV-2 infection. An asymptomatic infection includes both subjects who later go on to develop one or more symptoms, and subjects who never develop one or more symptoms.

An "effective amount" of a compound may vary according to factors such as the disease state, age, sex, and weight of the individual, and the ability of the compound to elicit the desired response. A therapeutically effective amount encompasses an amount in which any toxic or detrimental effects of the compound are outweighed by the therapeutically beneficial effects. An effective amount also encompasses an amount sufficient to confer benefit, e.g., clinical benefit.

The term "food," as used herein, refers to solid food with sufficient bulk and fat content that it is not rapidly dissolved and absorbed in the stomach. For example, a meal, such as breakfast, lunch, or dinner. The term "with food," as used herein refers to administration of a composition between about 30 minutes prior to to about two hours after eating, e.g., a meal. The terms "without food," "fasted," or "an empty stomach" refer to the condition of not having consumed solid food for at least about 2 hours after until about 30 minutes prior to consuming further solid food.

"Low-fat food" indicates a meal having no more than 25% of calories from fat. In some embodiments, the low-fat food contains about 11-14 g of fat. In some embodiments, the low-fat food contains about 400-500 total calories.

By "natural protein" is meant protein from a natural source (e.g., animal, plant, or fungus).

The term "pharmaceutical composition," as used herein, represents a composition containing a compound described herein formulated with a pharmaceutically acceptable excipient. Pharmaceutical compositions can be formulated, for example, for oral administration in unit dosage form (e.g., a tablet, capsule, caplet, gel cap, suspension, solution, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

As used herein, the term "pharmaceutically acceptable salt" means any salt that within the scope of sound medical judgment is suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

Frequently, the compounds are prepared or used as pharmaceutically acceptable salts prepared as addition products of pharmaceutically acceptable acids. Suitable pharmaceutically acceptable acids and methods for preparation of the appropriate salts are well-known in the art. Salts may be prepared from pharmaceutically acceptable non-toxic acids including inorganic and organic acids.

Representative acid addition salts include acetate, adipate, alginate, ascorbate, aspartate, benzenesulfonate, benzoate, besylate, bisulfate, borate, butyrate, camphorate, camphorsulfonate, citrate, cyclopentanepropionate, digluconate, dodecylsulfate, ethanesulfonate, fumarate, gentisate, glucoheptonate, glycerophosphate, glycolate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts.

As used herein, the term "substantially free" refers to the qualitative condition of exhibiting total or near-total extent or degree of the absence of a compound or type of compound of interest. One of ordinary skill in the biological arts will understand that biological and chemical phenomena rarely, if ever, can be determined to be zero without doubt, e.g., due to inherent error in any measurement. The term "substantially free" is therefore used herein to capture the potential lack of completeness inherent in many biological and chemical measurements.

As used herein, the term "subject" or "participant" or "patient" refers to any organism to which a compound or composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the subject; or enhancement or improvement of condition, disorder, or disease. Treatment includes eliciting a clinically significant response without excessive levels of side effects. Treatment also includes prolonging survival as compared to expected survival if not receiving treatment.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the description below. Other features, objects, and advantages of the invention will be apparent from the description and from the claims.

DETAILED DESCRIPTION

The present inventors have discovered that sepiapterin is effective in treating patients infected with SARS-CoV-2. In some embodiments, sepiapterin is effective in preventing the development of acute respiratory distress in SARS-CoV-2 patients. In some embodiments of any of the methods described herein, the method comprises preventing, delaying, or mitigating fibrotic disease resulting from acute respiratory distress. In some embodiments, the sepiapterin is administered with food. In some embodiments, the sepiapterin is administered without food. Without wishing to be bound by theory, sepiapterin may suppress inflammation in the lungs while simultaneously accelerating the development of the adaptive immune response that will resolve the infection. Accordingly, the present invention features methods for the treatment of SARS-CoV-2 infection in a subject by administering sepiapterin, or a pharmaceutically acceptable salt thereof.

The following description of sepiapterin activity is provided without wishing to be bound by theory.

Sepiapterin (SP) May Prevent Acute Respiratory Distress

Sepiapterin has been demonstrated in preclinical models to profoundly suppress innate immune cell mediated inflammation caused by Dextran Sulfate Sodium (DSS) (4) in the colon. Paradoxically, sepiapterin also enhances the proliferation rate of activated, mature CD8+ T cells (FIG. 2A), potentially through a separate mechanism. (5) Little is known about the pathogenesis of the acute respiratory symptoms caused by COVID-19.

Figure 1:
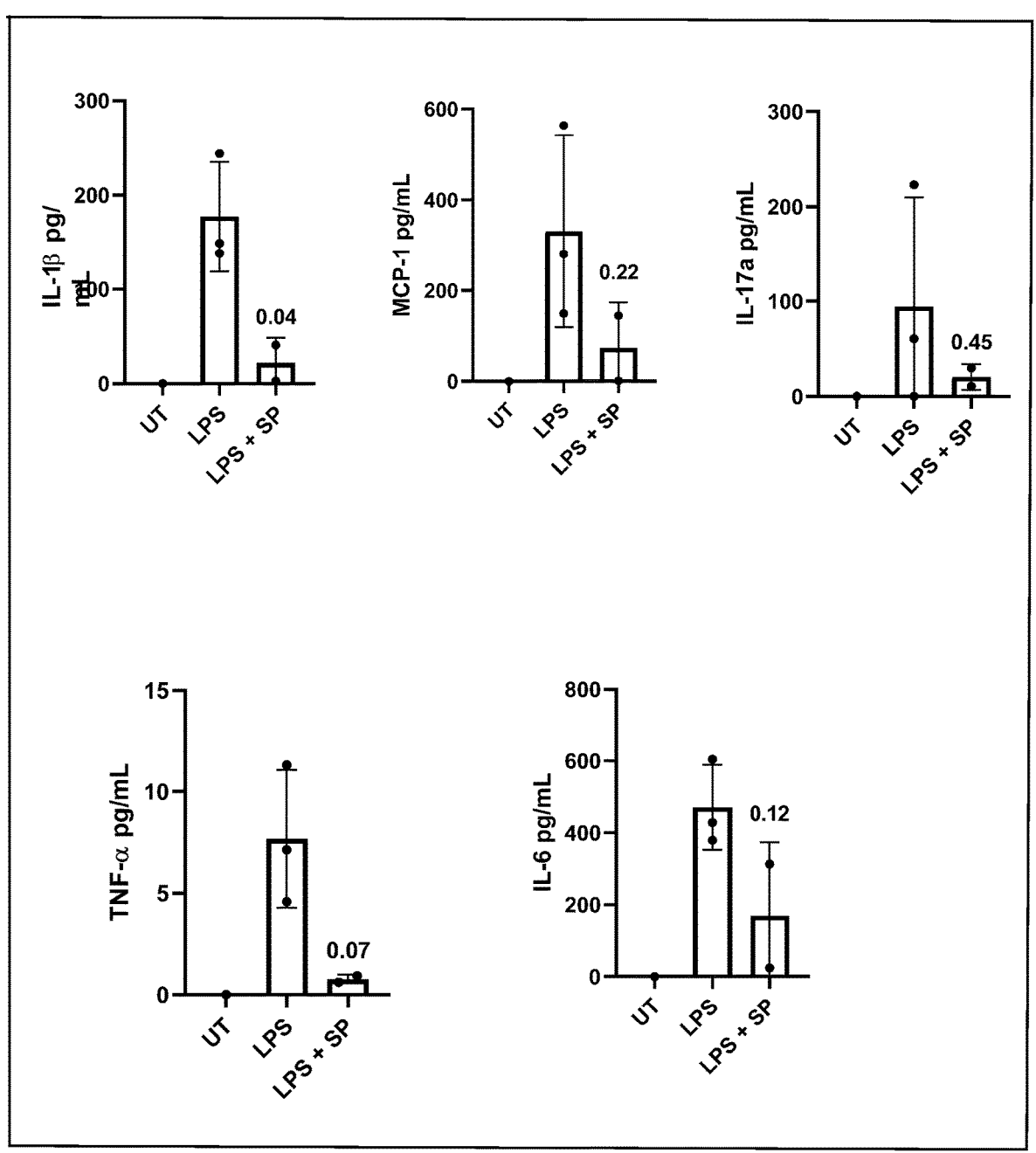
FIG. 1 is a graph showing cytokine expression in the lungs of mice treated with intranasal lipopolysaccharide (LPS) with or without 10 mg/kg sepiapterin (SP) treatment.

However, pathological reports suggest that it may be related to excessive activation of innate immune cells in the lungs by virally damaged cells, resulting in an acute respiratory distress syndrome (ARDS)-like illness. (2) Our data indicate that SP may limit inflammatory cytokine expression in the lungs in an in vivo model of ARDS (FIG. 1). This is in line with the therapeutic effect of SP in a Dextran Sulfate Sodium//Azoxymethane model of colitis/colon cancer. (4) Taken together, these data indicate that that SP can be used to limit innate immune stimulation initiated by various insults in different parts of the body, including the lungs.

Although the anti-inflammatory effect of SP treatment is only partially understood, much of its effects may be explained by the effects of nitric oxide synthase (NOS) "recoupling" and nitric oxide (NO) production and subsequent effect on the vasculature. NOS exhibits two alternative activities depending on the relative availability of its cofactor tetrahydrobiopterin (BH4). (7) In the presence of sufficient BH4, NOS catalyzes the production of NO and citrulline from the amino acid arginine. Within the active site of the enzyme, BH4 participates in the transfer of NADPH derived electrons to arginase, through a radical intermediate. (8,9) When the availability of BH4 is low, as it is in chronic inflammatory conditions (4) and tumors (10,11), electron transfer in the active site becomes uncoupled from the oxidation of arginine, resulting in the production of super oxide radical. (12,13) In the presence of trace amounts of NO, these two species react to form the short lived, tyrosine nitrating radical peroxynitrite. (14-16) When BH4 is available, NO production by endothelial NOS has an overall anti-inflammatory effect on the vasculature via activation of guanylate cyclase (sGC) and S-nitrosylation of individual proteins such as NF-κB. (17-18) When NOS is uncoupled, ROS/RNS stress as well as peroxynitrite mediated Tyr-nitration of IκBa (19) initiate endothelial dysfunction and potentiate vascular inflammation. Considering this, the inventors suggest that supplementation of BH4 levels with SP may limit inflammation and endothelial dysfunction in the lungs by reestablishing endothelial NO production and inhibiting NF-κB activation. Accordingly, in some embodiments, SP administration to subjects is begun as soon as they become symptomatic of the first phase of the disease in order to prevent the onset of acute respiratory symptoms through its anti-inflammatory action on the lungs.

Sepiapterin Enhances T-Cell Proliferation

Figure 2:
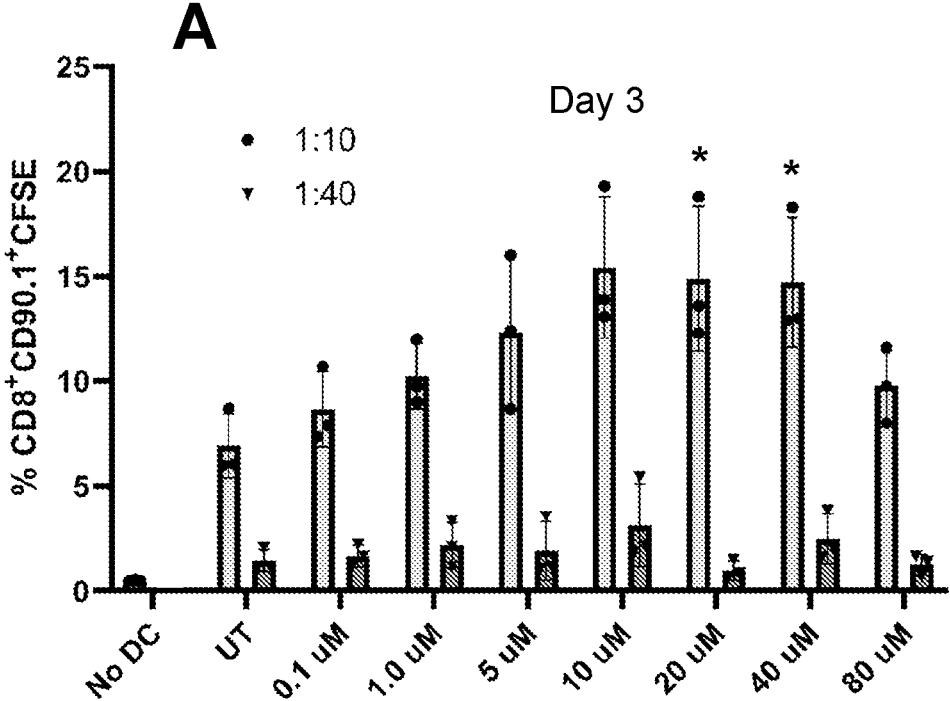
FIG. 2A is a graph showing the proliferation and activation of $CD8^+$ T cells in the presence of sepiapterin in vitro.
FIG. 2B is a graph showing cytokine (interferon gamma, IFN-γ) expression in cells in the presence of sepiapterin in vitro.
FIG. 2C is a graph showing cytokine (interleukin 2, IL-2) expression in cells in the presence of sepiapterin in vitro.
Figure 2:
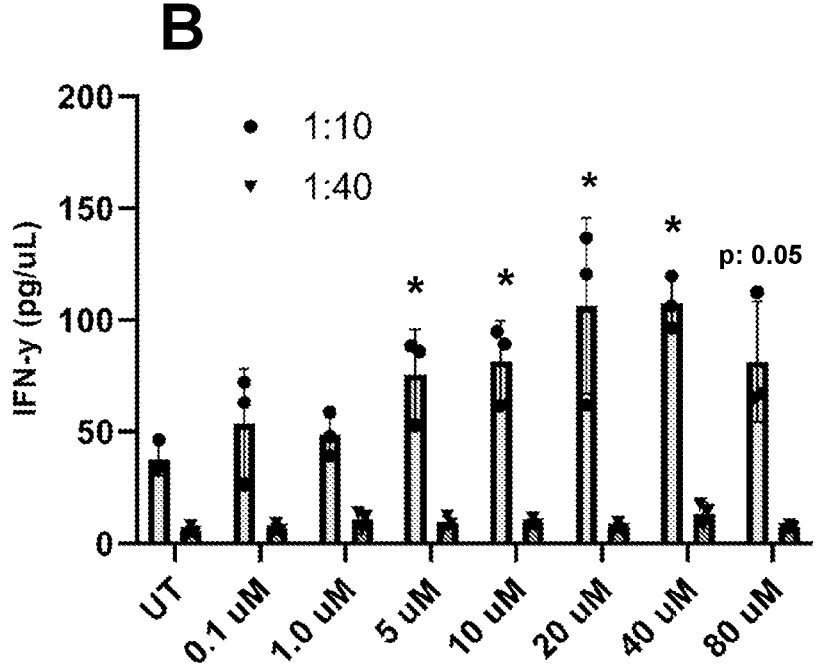
Figure 2:
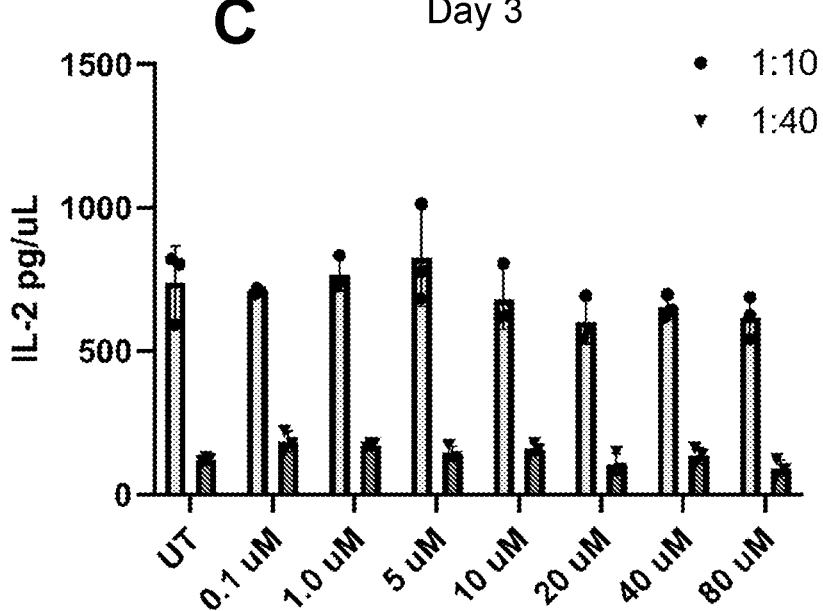
Figure 3:
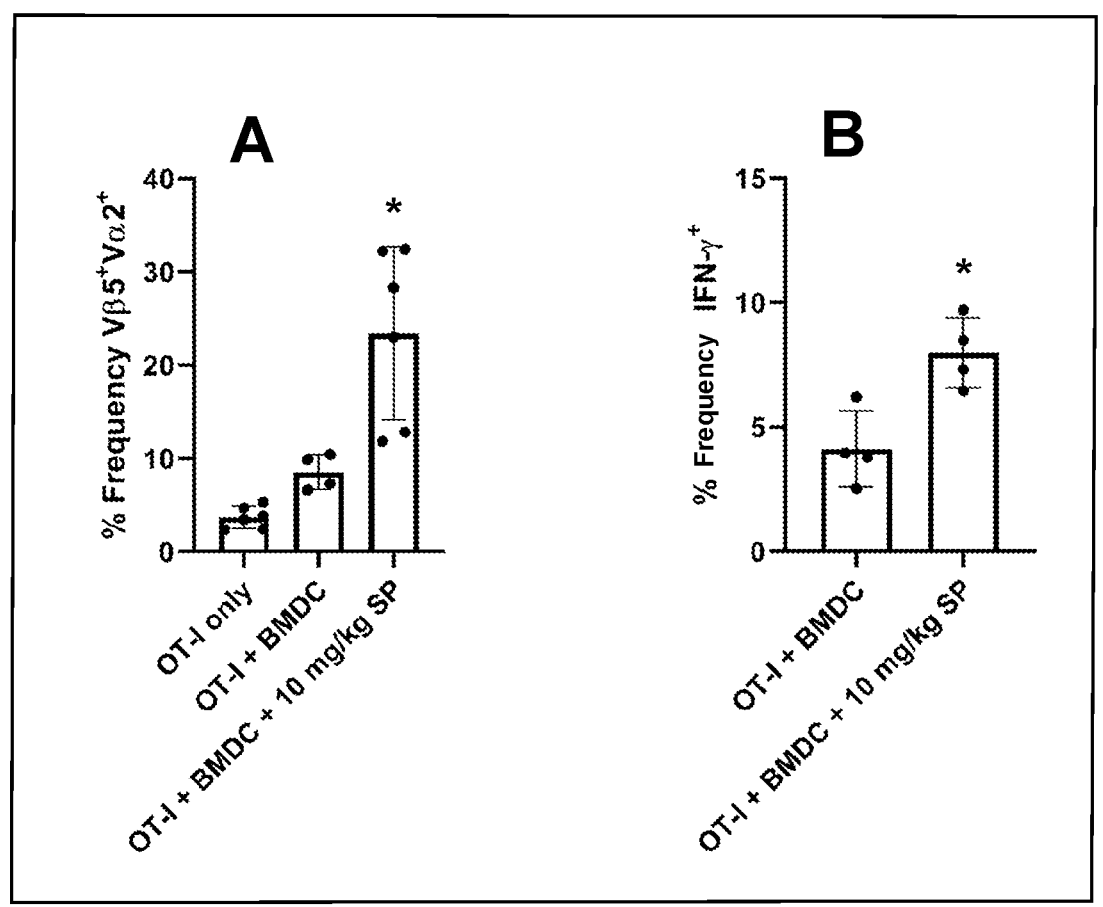
FIG. 3A is a graph showing the proliferation and activation of $CD8^+$ T cells in the presence of sepiapterin in vivo.
FIG. 3B is a graph showing cytokine (IFN-γ) expression in cells in the presence of sepiapterin in vivo.

High white blood cell (WBC) count in the presence of lymphocytopenia (low T cell count) is commonly observed in COVID-19 patients who develop severe symptoms. (3) This suggests that, for unknown reasons, these patients do not develop an adaptive immune response quickly enough to prevent progression to fulminate disease. We have demonstrated that sepiapterin supplementation enhances the proliferation of activated CD8+ T cells both in vitro (FIG. 2A) and in vivo (FIG. 3A). As such, SP may accelerate the adaptive immune response to SARS-CoV-2.

Under physiological conditions, the availability of BH4 has a rate limiting effect on T cell proliferation in a manner dependent upon the enhanced recycling of mitochondrial cytochrome c. (5) Pharmacological inhibition of sepiapterin reductase, the enzyme necessary for conversion of SP to BH4, has been used to successfully control multiple models of autoimmunity in vivo, demonstrating the critical role that BH4 availability has on T cell proliferation. (5) Importantly, while BH4 augmentation does influence T cell proliferation in multiple in vivo models, it does not directly impact T cell activation. In addition to this mechanism, low BH4 levels associated with chronic inflammation may also contribute to T cell dysfunction by inducing the uncoupling of endothelial nitric oxide synthase and the subsequent production of peroxynitrite radicals. (20-21) In addition to leading to the direct nitration and inactivation of the T cell receptor, peroxynitrite production has also been demonstrated to inhibit the activity of the chemokines CCL2 and CCLS, leading to T cell exclusion from tissues. (22-25) This may represent an avenue by which viruses and tumors evade elimination by the adaptive immune system. In summary, SP may enhance the anti-viral immune response affected by cytotoxic T cells through multiple mechanisms.

Sepiapterin is Well-Tolerated

Sepiapterin and BH4 supplementation has a well-established safety record in humans and causes no severe side effects, even at very high levels. This is in contrast to the anti-malarial drugs chloroquine and hydroxychloroquine, which have severe side effects and must be administered with supervision. Sepiapterin on the other hand has been shown to be well tolerated in clinical studies in healthy volunteers and in subjects with Phenylketonuria, Primary BH4 Deficiencies, or diabetic gastroparesis. (26) This is in stark contrast to almost all other drugs used for immuno-modulatory purposes.

T cell proliferation and cytokine production are usually coupled upon activation. Interventions such as pegylated IFN-α, pattern recognition receptor agonism, or immune checkpoint blockade typically enhance both the number and activation state of patient T cells. However, these therapies enhance T cell activity indiscriminately, putting patients at risk for off target autoimmune effects and severe reactions caused by T cell cytokine production. Due to its unique mechanism of action, SP enhances T cell proliferation without directly effecting T cell activation and IFN-γ secretion (5), making it a much safer immunomodulatory option compared to other global activators of T cell activity. The enhanced secretion of IFN-γ in FIG. 2B is a result of the higher number of T cells present in wells treated with SP. In addition, SP seems to only affect activated T cells that are actively proliferating, having already been presented with antigen and activated by APCs. Despite this effect on activated T cells, we know of no autoimmune or severe immune related events recorded in response to SP treatment. In some embodiments, SP is given to patients as soon as they begin to show symptoms of the early phase of the disease in order to combat lymphocytopenia, accelerate the adaptive immune response to SARS-CoV-2, and prophylactically protect patients from inflammation in the lungs.

Sepiapterin

Sepiapterin ((S)-2-amino-6-(2-hydroxypropanoyl)-7,8-dihydropteridin-4(3H)-one) passes into the cell and is converted to 7,8-dihydrobiopterin by sepiapterin reductase. 7,8-dihydrobiopterin is then converted to BH4 via reduction by dihydrofolate reductase.

Sepiapterin, or a pharmaceutically acceptable salt thereof, can be formulated in a pharmaceutical composition. In some embodiments, a pharmaceutical composition of the invention includes 20-30% sepiapterin, or a salt thereof, by total weight, e.g., about 20%, 22%, 25%, 27%, or 30%. In some embodiments, the pharmaceutical compositions include greater than 20% sepiapterin by total weight, e.g., greater than 25%, greater than 30%, greater than 40%, greater than 50%, greater than 60%, greater than 70%, greater than 80%, or greater than 90%. In some embodiments, the pharmaceutical composition includes less than 20% sepiapterin by total weight, e.g., less than 20%, less than 15%, less than 10%, or less than 5%.

In some embodiments, the invention features a pharmaceutical composition including sepiapterin, or a pharmaceutically acceptable salt thereof, and less than 10% by total weight of an antioxidant, e.g., about 9%, 7%, 5%, 3%, 1%, 0.5%, 0.25%, 0.1%, or no antioxidant. The antioxidant may be ascorbic acid. In some embodiments, the ratio of sepiapterin, or a pharmaceutically acceptable salt thereof, to the antioxidant is 1:1, or greater than 1:1, e.g., 2:1, 5:1, 7:1, or 10:1 by weight. The pharmaceutical composition may include 20-30% sepiapterin, or a pharmaceutically acceptable salt thereof, by total weight, e.g., about 20%, 22%, 25%, 27%, or 30%. The pharmaceutical composition can further include a dispersant, e.g., croscarmellose sodium. The pharmaceutical composition may include 0.1-1.5% dispersant by total weight, e.g., 0.1%, 0.5%, 1%, or 1.5%. In some embodiments, the pharmaceutical composition includes at least one anti-caking agent, e.g., colloidal silicon dioxide or microcrystalline cellulose. The pharmaceutical composition may include 65-75% anti-caking agent by total weight, e.g., about 65%, 67%, 70%, 73%, or 75%. In some embodiments, the pharmaceutical composition includes both colloidal silicon dioxide and microcrystalline cellulose. In some embodiments, the pharmaceutical composition includes 60-65% microcrystalline cellulose by total weight and 5-7% colloidal silicon dioxide by total weight. In some embodiments, the crystalline form of sepiapterin is formulated as particles less than 140 μm in size, e.g., about 120 μm, 110 μm, 100 μm, 90 μm, 80 μm, 70 μm, 60 μm, 50 μm, 40 μm, 30 μm, 20 μm, 10 μm, or 5 μm. In some embodiments, the pharmaceutical composition includes less than 1% of an impurity by total weight, such as lactoylpterin, e.g., the composition includes less than 0.9%, less than 0.8%, less than 0.7%, less than 0.6%, less than 0.5%, less than 0.4%, less than 0.3%, or less than 0.2%.

In some embodiments, the sepiapterin is a salt of sepiapterin, e.g., with sulfuric acid, p-toluene sulfonic acid, methane sulfonic acid, benzene sulfonic acid, malonic acid, tartaric acid (e.g., L-tartaric acid), phosphoric acid, gentisic acid, fumaric acid, glycolic acid, acetic acid, or nicotinic acid.

In some embodiments, the sepiapterin, or pharmaceutically acceptable salt thereof, is in crystalline form. The crystalline sepiapterin free base or a crystalline form of a salt of sepiapterin can occur as an anhydrate (e.g., without having any bound water or solvent or hydration or solvation) or as a hydrate, a partial hydrate (e.g., hemihydrate, sesquihydrate, and the like), as a dihydrate, a trihydrate, or the like, wherein the crystalline form binds a water of hydration or a solvent molecule associated with the crystalline form of sepiapterin or salt thereof. In an embodiment, crystalline sepiapterin occurs as a monohydrate or as a hemihydrate.

Exemplary salts, co-crystals, and crystalline forms of sepiapterin are described in WO 2018/102314, WO 2018/102315, WO 2019/232120, and WO 2019/046849, the crystalline forms, salts, and co-crystals of which are incorporated herein by reference in their entirety.

In some embodiments, the crystalline form of sepiapterin free base is crystalline Form F of sepiapterin free base and is characterized by an X-ray powder diffraction pattern obtained by irradiation with Cu Kα X-rays having peaks expressed as 2θ at 9.7°±0.5, e.g., 9.7°±0.2, 10.2°±0.5, e.g., 10.2°±0.2, and 11.3°±0.5, e.g., 11.3°±0.2. In other embodiments, the crystalline form of sepiapterin is characterized by an X-ray powder diffraction pattern obtained by irradiation with Cu Kα X-rays having peaks expressed as 2θ at 9.7°±0.5, e.g., 9.7°±0.2, 10.2°±0.5, e.g., 10.2°±0.2, 11.3°±0.5, e.g., 11.3°±0.2, 14.0°±0.5, e.g., 14.0°±0.2, 14.6°±0.5, e.g., 14.6°±0.2, 19.9°±0.5, e.g., 19.9°±0.2, 22.2°±0.5, e.g., 22.2°±0.2, 25.3°±0.5, e.g., 25.3°±0.2, and 32.4°±0.5, e.g., 32.4°±0.2. In an essentially pure form of this crystalline form, peaks can be observed at angles of refraction 2θ as set forth in Table 1. Alternatively or in addition, this crystalline form is characterized by a DSC curve showing two endotherms at 71.6° C. and 233.4° C.

TABLE 1

| Position [2θ°]<br>(±0.5, e.g., ±0.2) | Relative Intensity |
| --- | --- |
| 9.7 | 98.27 |
| 10.2 | 100.00 |
| 11.3 | 22.47 |
| 14.0 | 5.01 |
| 14.6 | 12.36 |
| 19.9 | 5.63 |
| 21.1 | 3.72 |
| 22.2 | 5.37 |
| 22.7 | 4.04 |
| 24.5 | 2.99 |
| 25.3 | 17.65 |
| 27.2 | 3.10 |
| 32.4 | 5.29 |
| 36.7 | 2.72 |

In some embodiments, the crystalline form of sepiapterin free base is crystalline Form B of sepiapterin free base and has peaks at diffraction angle 2θ (°) of 8.4°±0.5, e.g., 8.4°±0.2, 16.9°±0.5, e.g., 16.9°±0.2, and 25.4°±0.5, e.g., 25.4°±0.2 as measured by X-ray diffractometry by irradiation with Cu Kα X-rays or calculated from X-ray diffractometry. In some embodiments, the crystalline Form B of sepiapterin free base has peaks at diffraction angle 2θ (°) of 8.4°±0.5, e.g., 8.4°±0.2, 14.9°±0.5, e.g., 14.9°±0.2, 16.9°±0.5, e.g., 16.9°±0.2, 25.4°±0.5, e.g., 25.4°±0.2, and 34.1°±0.5, e.g., 34.1°±0.2 as measured by X-ray diffractometry by irradiation with Cu Kα X-rays or calculated from X-ray diffractometry. In an essentially pure material of this crystalline form, peaks can be observed at angles of refraction 2θ as set forth in Table 2. Alternatively, or in addition, this crystalline form is characterized by a DSC curve showing a melting event at 195.2° C.

TABLE 2

| Position [2θ°]<br>(±0.5, e.g., ±0.2) | Relative Intensity |
| --- | --- |
| 8.4 | 100.00 |
| 14.9 | 2.34 |
| 16.9 | 10.70 |
| 25.4 | 84.90 |
| 34.1 | 3.00 |

In some embodiments, the crystalline form of sepiapterin free base is crystalline Form C of sepiapterin free base and has peaks at diffraction angle 2θ (°) of 5.7°±0.5, e.g., 5.7°±0.2, 7.8°±0.5, e.g., 7.8°±0.2, and 25.4°±0.5, e.g., 25.4°±0.2 as measured by X-ray diffractometry by irradiation with Cu Kα X-rays or calculated from X-ray diffractometry. In some embodiments, the crystalline Form C of sepiapterin free base has peaks at diffraction angle 2θ (°) of 5.7°±0.5, e.g., 5.7°±0.2, 7.8°±0.5, e.g., 7.8°±0.2, 9.1°±0.5, e.g., 9.1°±0.2, 11.5°±0.5, e.g., 11.5°±0.2, 15.3°±0.5, e.g., 15.3°±0.2, 16.0°±0.5, e.g., 16.0°±0.2, 20.1°±0.5, e.g., 20.1°±0.2, 25.4°±0.5, e.g., 25.4°±0.2, and 26.6°±0.5, e.g., 26.6°±0.2, as measured by X-ray diffractometry by irradiation with Cu Kα X-rays or calculated from X-ray diffractometry. In an essentially pure material of this crystalline form, peaks can be observed at angles of refraction 2θ as set forth in Table 3. Alternatively or in addition, this crystalline form is characterized by a DSC curve showing five endothermal peaks at 58.3° C., 101.8° C., 129.8° C., 156.5° C., and 168.3° C.

TABLE 3

| Position [2θ°]<br>(±0.5, e.g., ±0.2) | Relative Intensity |
| --- | --- |
| 5.7 | 48.91 |
| 7.8 | 100.00 |
| 9.1 | 59.49 |
| 10.4 | 8.72 |
| 11.5 | 24.53 |
| 12.9 | 8.50 |
| 14.8 | 9.24 |
| 15.3 | 12.53 |
| 16.0 | 14.09 |
| 17.2 | 7.22 |
| 18.2 | 4.25 |
| 19.2 | 5.78 |
| 20.1 | 14.54 |
| 21.5 | 6.47 |
| 22.9 | 6.85 |
| 23.7 | 4.80 |
| 25.4 | 65.68 |
| 26.6 | 14.53 |

TABLE 3-continued

| Position [2θ°] (±0.5, e.g., ±0.2) | Relative Intensity |
|---|---|
| 27.4 | 8.39 |
| 31.5 | 3.74 |
| 34.2 | 4.36 |

In some embodiments, the crystalline form of sepiapterin free base is crystalline Form D of sepiapterin free base and has peaks at diffraction angle 2θ (°) of 8.9°±0.5, e.g., 8.9°±0.2, 10.3°±0.5, e.g., 10.3°±0.2, and 26.0°±0.5, e.g., 26.0°±0.2, as measured by X-ray diffractometry by irradiation with Cu Kα X-rays or calculated from X-ray diffractometry. In some embodiments, the crystalline Form D of sepiapterin free base has peaks at diffraction angle 2θ (°) of 8.9°±0.5, e.g., 8.9°±0.2, 10.3°±0.5, e.g., 10.3°±0.2, 10.9°±0.5, e.g., 10.9°±0.2, 17.8°±0.5, e.g., 17.8°±0.2, 24.9°±0.5, e.g., 24.9°±0.2, 26.0°±0.5, e.g., 26.0°±0.2, 26.7°±0.5, e.g., 26.7°±0.2, 26.8°±0.5, e.g., 26.8°±0.2, and 28.3°±0.5, e.g., 28.3°±0.2, as measured by X-ray diffractometry by irradiation with Cu Kα X-rays or calculated from X-ray diffractometry. In an essentially pure material of this crystalline form, peaks can be observed at angles of refraction 2θ as set forth in Table 4. Alternatively or in addition, this crystalline form is characterized by a DSC curve showing three endotherms at 42.7° C., 66.3° C., and 232.9° C.

TABLE 4

| Position [2θ°] (±0.5, e.g., ±0.2) | Relative Intensity |
|---|---|
| 8.9 | 100.00 |
| 10.3 | 49.92 |
| 10.9 | 19.96 |
| 11.6 | 2.15 |
| 13.6 | 2.99 |
| 14.2 | 3.45 |
| 14.8 | 2.35 |
| 15.4 | 2.59 |
| 16.4 | 1.55 |
| 17.2 | 2.33 |
| 17.8 | 6.24 |
| 19.6 | 2.62 |
| 20.1 | 2.28 |
| 20.5 | 3.09 |
| 20.8 | 2.27 |
| 21.3 | 3.60 |
| 22.3 | 4.79 |
| 23.7 | 4.31 |
| 24.9 | 5.19 |
| 26.0 | 41.94 |
| 26.7 | 8.58 |
| 26.8 | 9.17 |
| 27.4 | 3.98 |
| 28.3 | 4.75 |
| 28.7 | 6.60 |
| 29.8 | 3.03 |
| 31.8 | 2.72 |
| 33.0 | 2.03 |
| 35.5 | 1.57 |
| 37.1 | 1.09 |

In some embodiments, the crystalline form of sepiapterin free base is crystalline Form A of sepiapterin free base and has peaks at diffraction angle 2θ (°) of 4.7°±0.5, e.g., 4.7°±0.2, 7.4°±0.5, e.g., 7.4°±0.2, and 26.2°±0.5, e.g., 26.2°±0.2, as measured by X-ray diffractometry by irradiation with Cu Kα X-rays or calculated from X-ray diffractometry. In some embodiments, the crystalline Form A of sepiapterin free base has peaks at diffraction angle 2θ (°) of 4.7°±0.5, e.g., 4.7°±0.2, 7.4°±0.5, e.g., 7.4°±0.2, 9.5°±0.5, e.g., 9.5°±0.2, 11.3°±0.5, e.g., 11.3°±0.2, 15.6°±0.5, e.g., 15.6°±0.2, 16.4°±0.5, e.g., 16.4°±0.2, 26.2°±0.5, e.g., 26.2°±0.2, and 27.2°±0.5, e.g., 27.2°±0.2 as measured by X-ray diffractometry by irradiation with Cu Kα X-rays or calculated from X-ray diffractometry. In an essentially pure material of this crystalline form, peaks can be observed at angles of refraction 2θ as set forth in Table 5. Alternatively, or in addition, this crystalline form is characterized by a DSC curve showing endothermal peaks at 82.8° C. and 179.8° C.

TABLE 5

| Position [2θ°] (±0.5, e.g., ±0.2) | Relative Intensity |
|---|---|
| 4.7 | 47.76 |
| 7.4 | 100.00 |
| 9.5 | 33.54 |
| 11.3 | 19.31 |
| 12.4 | 8.49 |
| 13.4 | 3.60 |
| 14.2 | 8.24 |
| 15.6 | 15.08 |
| 16.4 | 11.97 |
| 17.6 | 8.35 |
| 18.4 | 5.03 |
| 19.8 | 9.18 |
| 21.5 | 5.44 |
| 24.4 | 5.56 |
| 26.2 | 35.37 |
| 27.2 | 19.11 |
| 28.9 | 5.93 |

In some embodiments, the crystalline form of sepiapterin free base is crystalline Form E of sepiapterin free base and has at peaks at diffraction angle 2θ (°) of 6.0°±0.5, 6.0°±0.2 10.6°±0.5, 10.6°±0.2, 12.1°±0.5, e.g., 12.1°±0.2, 15.9°±0.5, e.g., 15.9°±0.2, 20.9°±0.5, e.g., 20.9°±0.2, and 24.6°±0.5, e.g., 24.6°±0.2, as measured by X-ray diffractometry by irradiation with Cu Kα X-rays or calculated from X-ray diffractometry. In some embodiments, the crystalline Form E of sepiapterin free base has peaks at diffraction angle 2θ (°) of 6.0°±0.5, e.g., 6.0°±0.2, 10.6°±0.5, e.g., 10.6°±0.2, 12.1°±0.5, e.g., 12.1°±0.2, 15.9°±0.5, e.g., 15.9°±0.2, 18.1°±0.5, e.g., 18.1°±0.2, 20.9°±0.5, e.g., 20.9°±0.2, 22.1°±0.5, e.g., 22.1°±0.2, 24.6°±0.5, e.g., 24.6°±0.2, 26.1°±0.5, e.g., 26.1°±0.2, 28.1°±0.5, e.g., 28.1°±0.2, 28.9°±0.5, e.g., 28.9°±0.2, 32.1°±0.5, e.g., 32.1°±0.2, and 37.0°±0.5, e.g., 37.0°±0.2 as measured by X-ray diffractometry by irradiation with Cu Kα X-rays or calculated from X-ray diffractometry. In an essentially pure form of this crystalline form, peaks can be observed at angles of refraction 2θ as set forth in Table 6. Alternatively or in addition, this crystalline form is characterized by a DSC curve showing two endothermal peaks at 112.9° C. and 195.8° C.

TABLE 6

| Position [2θ°] (±0.5, e.g., ±0.2) | Relative Intensity |
|---|---|
| 6.0 | 100.00 |
| 10.6 | 20.78 |
| 12.1 | 31.95 |
| 15.9 | 12.83 |
| 18.1 | 3.39 |
| 20.9 | 11.63 |
| 22.1 | 2.79 |
| 24.6 | 8.28 |
| 26.1 | 0.88 |
| 28.1 | 7.33 |

TABLE 6-continued

| Position [2θ°] (±0.5, e.g., ±0.2) | Relative Intensity |
|---|---|
| 28.9 | 3.77 |
| 32.1 | 3.57 |
| 37.0 | 1.03 |

In some embodiments, the crystalline form of sepiapterin free base is crystalline Form G of sepiapterin free base and has peaks at diffraction angle 2θ (°) of 10.0°±0.5, e.g., 10.0°±0.2, 10.6°±0.5, e.g., 10.6°±0.2, and 25.7°±0.5, e.g., 25.7°±0.2, as measured by X-ray diffractometry by irradiation with Cu Kα X-rays or calculated from X-ray diffractometry. In some embodiments, the Form G of sepiapterin free base has peaks at diffraction angle 2θ (°) of 10.0°±0.5, e.g., 10.0°±0.2, 10.6°±0.5, e.g., 10.6°±0.2, 11.2°±0.5, e.g., 11.2°±0.2, 15.3°±0.5, e.g., 15.3°±0.2, 15.9°±0.5, e.g., 15.9°±0.2, 22.8°±0.5, e.g., 22.8°±0.2, 24.4°±0.5, e.g., 24.4°±0.2, 25.0°±0.5, e.g., 25.0°±0.2, 25.7°±0.5, e.g., 25.7°±0.2, and 26.6°±0.5, e.g., 26.6°±0.2 as measured by X-ray diffractometry by irradiation with Cu Kα X-rays or calculated from X-ray diffractometry. In an essentially pure material of this crystalline form, peaks can be observed at angles of refraction 2θ as set forth in Table 7.

TABLE 7

| Position [2θ°] (±0.5, e.g., ±0.2) | Relative Intensity |
|---|---|
| 5.3 | 8.30 |
| 6.9 | 4.54 |
| 10.0 | 100.00 |
| 10.6 | 69.64 |
| 11.2 | 6.59 |
| 13.5 | 7.52 |
| 15.3 | 26.59 |
| 15.9 | 26.43 |
| 16.0 | 23.41 |
| 16.9 | 4.28 |
| 18.6 | 13.02 |
| 19.3 | 11.90 |
| 20.1 | 7.22 |
| 20.8 | 11.01 |
| 22.8 | 16.77 |
| 23.5 | 19.60 |
| 24.4 | 41.45 |
| 25.0 | 23.99 |
| 25.7 | 65.40 |
| 26.6 | 39.64 |
| 27.6 | 13.04 |
| 28.7 | 6.55 |
| 30.8 | 14.76 |
| 32.2 | 9.63 |
| 33.7 | 5.16 |
| 37.5 | 5.80 |

In some embodiments, the crystalline form of the hydrochloride salt of sepiapterin has peaks at diffraction angle 2θ (°) of 7.8°±0.5, e.g., 7.8°±0.2, 12.9°±0.5, e.g., 12.9°±0.2, and 26.2°±0.5, e.g., 26.2°±0.2, as measured by X-ray diffractometry by irradiation with Cu Kα X-rays or calculated from X-ray diffractometry. In some embodiments, the most intense peak in the X-ray diffraction diagram of the crystalline form of the hydrochloride salt of sepiapterin is observed at an angle of refraction 2θ of 7.8°±0.5, e.g., 7.8°±0.2. In an essentially pure material of this crystalline hydrochloride salt of sepiapterin, peaks can be observed at angles of refraction 2θ as set forth in Table 8. Alternatively or in addition, the crystalline hydrochloride salt of sepiapterin is characterized by a DSC curve showing an endotherm at 225.9° C.

TABLE 8

| Position [2θ°] (±0.5, e.g., ±0.2) | Relative Intensity |
|---|---|
| 7.8 | 100.00 |
| 8.9 | 6.89 |
| 12.9 | 58.56 |
| 15.6 | 8.52 |
| 17.9 | 25.23 |
| 19.2 | 5.48 |
| 21.1 | 10.97 |
| 23.6 | 25.15 |
| 25.2 | 22.66 |
| 26.2 | 45.91 |
| 27.6 | 32.94 |
| 30.3 | 10.50 |
| 31.7 | 7.83 |
| 34.2 | 8.87 |
| 36.7 | 3.67 |

In some embodiments, the crystalline Form 1 methanesulfonate salt of sepiapterin has peaks at diffraction angle 2θ (°) of 7.8°±0.5, e.g., 7.8°±0.2, 23.5°±0.5, e.g., 23.5°±0.2, and 29.0°±0.5, e.g., 29.0°±0.2 as measured by X-ray diffractometry by irradiation with Cu Kα X-rays or calculated from X-ray diffractometry. In some embodiments, the most intense peak in the X-ray diffraction diagram is observed at an angle of refraction 2θ of 23.5°±0.5, e.g., 23.5°±0.2. In an essentially pure material of the crystalline Form 1 methanesulfonate salt of sepiapterin, peaks can be observed at angles of refraction 2θ as set forth in Table 9. Alternatively or in addition, the crystalline form 1 methanesulfonate salt of sepiapterin is characterized by a DSC curve showing two endotherms at 186.0° C. and 229.1° C.

TABLE 9

| Position [2θ°] (±0.5, e.g., ±0.2) | Relative Intensity |
|---|---|
| 7.9 | 21.77 |
| 11.7 | 8.20 |
| 13.7 | 8.52 |
| 15.7 | 4.79 |
| 16.6 | 5.34 |
| 18.0 | 5.66 |
| 19.8 | 2.10 |
| 20.3 | 5.36 |
| 20.9 | 2.43 |
| 22.3 | 4.25 |
| 22.7 | 2.15 |
| 23.5 | 100.00 |
| 24.7 | 3.69 |
| 25.6 | 2.70 |
| 26.8 | 1.79 |
| 27.2 | 1.68 |
| 28.3 | 2.75 |
| 29.0 | 57.60 |
| 29.8 | 5.18 |
| 30.5 | 1.37 |
| 32.2 | 4.66 |
| 33.0 | 1.64 |
| 36.5 | 1.29 |

In some embodiments, the crystalline Form 2 methanesulfonate salt of sepiapterin has peaks at diffraction angle 2θ (°) of 7.9°±0.5, e.g., 7.9°±0.2, 23.4°±0.5, e.g., 23.4°±0.2, and 28.9°±0.5, e.g., 28.9°±0.2 as measured by X-ray diffractometry by irradiation with Cu Kα X-rays or calculated from X-ray diffractometry. In some embodiments, the most intense peak in the X-ray diffraction diagram is observed at an angle of refraction 2θ of 7.9°±0.5, e.g., 7.9°±0.2. In an essentially pure material of the crystalline Form 2 methanesulfonate salt of sepiapterin, peaks can be observed at angles of refraction 2θ as set forth in Table 10. Alternatively or in addition, the crystalline form 2 methanesulfonate salt of sepiapterin is characterized by a DSC curve showing three endotherms at 75.5° C., 182.6° C., and 234.9° C.

TABLE 10

| Position [2θ°] (±0.5, e.g., ±0.2) | Relative Intensity |
|---|---|
| 7.9 | 100.00 |
| 11.0 | 21.32 |
| 12.1 | 22.02 |
| 13.5 | 79.87 |
| 15.7 | 11.87 |
| 17.8 | 9.81 |
| 19.7 | 10.93 |
| 21.3 | 26.79 |
| 23.4 | 96.13 |
| 24.1 | 24.88 |
| 24.3 | 22.10 |
| 25.5 | 9.45 |
| 26.0 | 11.27 |
| 27.6 | 7.63 |
| 28.9 | 95.64 |
| 31.2 | 4.39 |
| 36.1 | 6.65 |

In some embodiments, the crystalline Form 3 methanesulfonate salt of sepiapterin has peaks at diffraction angle 2θ (°) of 21.7°±0.5, e.g., 21.7°±0.2, 26.1°±0.5, e.g., 26.1°±0.2, and 28.9°±0.5, e.g., 28.9°±0.2 as measured by X-ray diffractometry by irradiation with Cu Kα X-rays or calculated from X-ray diffractometry. In some embodiments, the most intense peak in the X-ray diffraction diagram is observed at an angle of refraction 2θ of 26.1°±0.5, e.g., 26.1°±0.2. In an essentially pure material of the crystalline Form 3 methanesulfonate salt of sepiapterin, peaks can be observed at angles of refraction 2θ as set forth in Table 11. Alternatively or in addition, the crystalline form 3 methanesulfonate salt of sepiapterin is characterized by a DSC curve showing two endotherms at 195.1° C. and 240.1° C.

TABLE 11

| Position [2θ°] (±0.5, e.g., ±0.2) | Relative Intensity |
|---|---|
| 8.2 | 47.29 |
| 10.8 | 56.14 |
| 12.6 | 16.34 |
| 13.2 | 15.90 |
| 14.0 | 24.39 |
| 15.0 | 12.03 |
| 15.9 | 16.20 |
| 18.2 | 22.97 |
| 20.1 | 25.53 |
| 20.5 | 14.97 |
| 21.3 | 22.70 |
| 21.7 | 71.48 |
| 22.2 | 11.40 |
| 23.6 | 46.37 |
| 24.8 | 44.00 |
| 25.5 | 9.08 |
| 26.1 | 100.00 |
| 27.3 | 3.52 |
| 28.9 | 68.42 |
| 31.2 | 4.49 |
| 32.1 | 6.48 |
| 34.8 | 5.95 |
| 35.6 | 1.67 |
| 39.1 | 2.91 |

In some embodiments, the crystalline nicotinate salt of sepiapterin has peaks at diffraction angle 2θ (°) of 9.5°±0.5, e.g., 9.5°±0.2, 9.9°±0.5, e.g., 9.9°±0.2, and 24.5°±0.5, e.g., 24.5°±0.2 as measured by X-ray diffractometry by irradiation with Cu Kα X-rays or calculated from X-ray diffractometry. In some embodiments, the most intense peak in the X-ray diffraction diagram is observed at an angle of refraction 2θ of 24.5°±0.5, e.g., 24.5°±0.2. In an essentially pure material of the crystalline nicotinate salt of sepiapterin, peaks can be observed at angles of refraction 2θ as set forth in Table 12. Alternatively or in addition, the crystalline nicotinate salt of sepiapterin is characterized by a DSC curve showing an endotherm at 221.9° C.

TABLE 12

| Position [2θ°] (±0.5, e.g., ±0.2) | Relative Intensity |
|---|---|
| 9.5 | 10.29 |
| 9.9 | 53.95 |
| 11.5 | 9.31 |
| 12.0 | 11.76 |
| 14.7 | 14.20 |
| 15.9 | 17.61 |
| 17.5 | 7.53 |
| 19.0 | 5.37 |
| 20.8 | 5.88 |
| 21.3 | 6.12 |
| 21.7 | 7.20 |
| 23.2 | 34.05 |
| 24.5 | 100.00 |
| 25.2 | 12.90 |
| 28.0 | 8.51 |
| 31.1 | 5.39 |
| 32.3 | 4.52 |
| 33.4 | 8.02 |
| 35.1 | 5.05 |

In some embodiments, the crystalline p-toluenesulfonate salt of has peaks at diffraction angle 2θ (°) of 6.5°±0.5, e.g., 6.5°±0.2, 15.1°±0.5, e.g., 15.1°±0.2, and 23.4°±0.5, e.g., 23.4°±0.2 as measured by X-ray diffractometry by irradiation with Cu Kα X-rays or calculated from X-ray diffractometry. In some embodiments, the most intense peak in the X-ray diffraction diagram is observed at an angle of refraction 2θ of 6.5°±0.5, e.g., 6.5°±0.2. In an essentially pure material of the p-toluenesulfonate salt of sepiapterin, peaks can be observed at angles of refraction 2θ as set forth in Table 13. Alternatively or in addition, the crystalline p-toluenesulfonate salt of sepiapterin is characterized by a DSC curve showing three endotherms at 77.2° C., 202.4° C. and 260.2° C.

TABLE 13

| Position [2θ°] (±0.5, e.g., ±0.2) | Relative Intensity |
|---|---|
| 6.5 | 100.00 |
| 12.9 | 1.79 |
| 14.3 | 1.39 |
| 15.1 | 15.36 |
| 16.2 | 5.33 |
| 18.4 | 8.96 |
| 19.6 | 3.06 |
| 20.2 | 4.86 |
| 21.8 | 2.23 |
| 22.5 | 2.95 |
| 23.1 | 7.99 |
| 23.4 | 9.14 |
| 24.5 | 1.81 |
| 26.0 | 2.48 |
| 27.0 | 4.49 |
| 27.3 | 3.93 |
| 28.1 | 5.31 |
| 28.4 | 5.59 |

TABLE 13-continued

| Position [2θ°] (±0.5, e.g., ±0.2) | Relative Intensity |
|---|---|
| 28.8 | 2.05 |
| 30.6 | 2.24 |
| 31.0 | 1.98 |
| 32.6 | 1.82 |

In some embodiments, the crystalline benzenesulfonate salt of sepiapterin has peaks at diffraction angle 2θ (°) of 6.5°±0.5, e.g., 6.5°±0.2, 14.8°±0.5, e.g., 14.8°±0.2, and 19.6°±0.5, e.g., 19.6°±0.2 as measured by X-ray diffractometry by irradiation with Cu Kα X-rays or calculated from X-ray diffractometry. In some embodiments, the most intense peak in the X-ray diffraction diagram is observed at an angle of refraction 2θ of 6.5°±0.5, e.g., 6.5°±0.2. In an essentially pure material of the benzenesulfonate salt of sepiapterin, peaks can be observed at angles of refraction 2θ as set forth in Table 14. Alternatively or in addition, the crystalline benzenesulfonate salt of sepiapterin is characterized by a DSC curve showing two endotherms at 202.3° C. and 265.5° C.

TABLE 14

| Position [2θ°] (±0.5, e.g., ±0.2) | Relative Intensity |
|---|---|
| 4.9 | 5.90 |
| 6.5 | 100.00 |
| 14.8 | 16.73 |
| 17.8 | 4.23 |
| 19.6 | 7.98 |
| 21.5 | 2.49 |
| 23.7 | 3.46 |
| 24.5 | 3.84 |
| 26.1 | 3.29 |

In some embodiments, the crystalline phosphate salt of sepiapterin has peaks at diffraction angle 2θ (°) of 16.6°±0.5, e.g., 16.6°±0.2, 22.2°±0.5, e.g., 22.2°±0.2, and 25.6°±0.5, e.g., 25.6°±0.2 as measured by X-ray diffractometry by irradiation with Cu Kα X-rays or calculated from X-ray diffractometry.

In some embodiments, the most intense peak in the X-ray diffraction diagram is observed at an angle of refraction 2θ of 25.6°±0.5, e.g., 25.6°±0.2. In an essentially pure material of the crystalline phosphate salt of sepiapterin, peaks can be observed at angles of refraction 2θ as set forth in Table 15. Alternatively or in addition, the crystalline phosphate salt of sepiapterin is characterized by a DSC curve showing three endotherms at 125.9° C., 152.1° C., and 157.6° C.

TABLE 15

| Position [2θ°] (±0.5, e.g., ±0.2) | Relative Intensity |
|---|---|
| 5.5 | 4.41 |
| 8.1 | 1.21 |
| 8.9 | 2.21 |
| 10.3 | 1.79 |
| 10.8 | 5.80 |
| 15.3 | 1.84 |
| 16.6 | 8.35 |
| 17.7 | 1.95 |
| 20.3 | 1.40 |
| 21.2 | 1.61 |
| 22.2 | 9.77 |
| 23.1 | 1.74 |

TABLE 15-continued

| Position [2θ°] (±0.5, e.g., ±0.2) | Relative Intensity |
|---|---|
| 25.6 | 100.00 |
| 30.8 | 6.31 |
| 31.1 | 4.85 |
| 33.5 | 0.73 |
| 36.0 | 1.70 |

In some embodiments, the crystalline malonate salt of sepiapterin has peaks at diffraction angle 2θ (°) of 6.9°±0.5, e.g., 6.9°±0.2, 22.7°±0.5, e.g., 22.7°±0.2 and 23.8°±0.5, e.g., 23.8°±0.2 as measured by X-ray diffractometry by irradiation with Cu Kα X-rays or calculated from X-ray diffractometry. In some embodiments, the most intense peak in the X-ray diffraction diagram is observed at an angle of refraction 2θ of 6.9°±0.5, e.g., 6.9°±0.2. In an essentially pure material of the crystalline malonate salt of sepiapterin, peaks can be observed at angles of refraction 2θ as set forth in Table 16. Alternatively or in addition, the crystalline malonate salt of sepiapterin is characterized by a DSC curve showing a melting event at 115.8° C.

TABLE 16

| Position [2θ°] (±0.5, e.g., ±0.2) | Relative Intensity |
|---|---|
| 6.9 | 100.00 |
| 8.4 | 13.11 |
| 10.6 | 7.62 |
| 16.4 | 5.63 |
| 17.8 | 9.73 |
| 19.3 | 8.96 |
| 20.1 | 9.99 |
| 22.2 | 10.50 |
| 22.7 | 20.52 |
| 23.8 | 34.02 |
| 24.5 | 5.82 |
| 25.5 | 24.50 |
| 26.6 | 4.00 |
| 27.3 | 6.96 |
| 29.8 | 5.38 |
| 33.1 | 12.08 |

In some embodiments, the crystalline L-tartrate salt of sepiapterin has peaks at diffraction angle 2θ (°) of 7.4°±0.5, e.g., 7.4°±0.2, 14.2°±0.5, e.g., 14.2°±0.2, and 21.8°±0.5, e.g., 21.8°±0.2 as measured by X-ray diffractometry by irradiation with Cu Kα X-rays or calculated from X-ray diffractometry. In some embodiments, the most intense peak in the X-ray diffraction diagram is observed at an angle of refraction 2θ of 7.4°±0.5, e.g., 7.4°±0.2. In an essentially pure material of the crystalline L-tartrate salt of sepiapterin, peaks can be observed at angles of refraction 2θ as set forth in Table 17. Alternatively or in addition, the crystalline L-tartrate salt of sepiapterin is characterized by a DSC curve showing two endotherms at 97.2° C. and 160.6° C.

TABLE 17

| Position [2θ°] (±0.5, e.g., ±0.2) | Relative Intensity |
|---|---|
| 7.4 | 100.00 |
| 10.1 | 47.99 |
| 14.2 | 82.76 |
| 14.7 | 27.06 |
| 19.1 | 21.16 |
| 20.2 | 29.91 |
| 21.8 | 85.30 |

TABLE 17-continued

| Position [2θ°] (±0.5, e.g., ±0.2) | Relative Intensity |
|---|---|
| 22.1 | 53.68 |
| 23.9 | 85.30 |
| 24.9 | 19.26 |
| 25.5 | 28.45 |
| 26.8 | 18.58 |
| 29.7 | 21.59 |
| 31.6 | 10.10 |
| 32.9 | 22.18 |

In some embodiments, the crystalline gentisate salt of sepiapterin has peaks at diffraction angle 2θ (°) of 7.1°±0.5, e.g., 7.1°±0.2, 8.7°±0.5, e.g., 8.7°±0.2, and 26.7°±0.5, e.g., 26.7°±0.2 as measured by X-ray diffractometry by irradiation with Cu Kα X-rays or calculated from X-ray diffractometry. In some embodiments the most intense peak in the X-ray diffraction diagram is observed at an angle of refraction 2θ of 7.1°±0.5, e.g., 7.1°±0.2. In an essentially pure material of the crystalline gentisate salt of sepiapterin, peaks can be observed at angles of refraction 2θ as set forth in Table 18. Alternatively or in addition, the crystalline gentisate salt of sepiapterin is characterized by a DSC curve showing three endotherms at 70.5° C., 128.2° C., and 184.7° C.

TABLE 18

| Position [2θ°] (±0.5, e.g., ±0.2) | Relative Intensity |
|---|---|
| 5.7 | 17.29 |
| 7.1 | 100.00 |
| 8.7 | 42.69 |
| 10.4 | 3.94 |
| 11.3 | 11.69 |
| 12.1 | 4.13 |
| 14.3 | 21.10 |
| 16.0 | 6.46 |
| 16.4 | 5.94 |
| 17.0 | 5.85 |
| 17.6 | 7.93 |
| 19.1 | 8.27 |
| 20.20 | 3.47 |
| 20.7 | 2.90 |
| 21.5 | 3.37 |
| 23.6 | 2.69 |
| 24.4 | 4.50 |
| 26.7 | 52.20 |
| 27.1 | 35.49 |
| 28.2 | 8.74 |
| 28.9 | 4.31 |
| 29.9 | 2.62 |
| 31.4 | 2.99 |
| 34.4 | 1.28 |
| 35.8 | 3.54 |
| 37.6 | 0.57 |

In some embodiments, the crystalline fumarate salt of sepiapterin has peaks at diffraction angle 2θ (°) of 11.4°±0.5, e.g., 11.4°±0.2, 24.0°±0.5, e.g., 24.0°±0.2, and 28.2°±0.5, e.g., 28.2°±0.2 as measured by X-ray diffractometry by irradiation with Cu Kα X-rays or calculated from X-ray diffractometry. In some embodiments, the most intense peak in the X-ray diffraction diagram is observed at an angle of refraction 2θ of at least 24.0°±0.5, e.g., 24.0°±0.2. In an essentially pure material of the crystalline fumarate salt of sepiapterin, peaks can be observed at angles of refraction 2θ as set forth in Table 19. Alternatively or in addition, crystalline fumarate salt of sepiapterin is characterized by a DSC curve showing two endotherms at 114.3° C. and 229.7° C.

TABLE 19

| Position [2θ°] (±0.5, e.g., ±0.2) | Relative Intensity |
|---|---|
| 6.1 | 6.43 |
| 7.7 | 5.40 |
| 11.4 | 53.62 |
| 11.9 | 33.37 |
| 14.2 | 8.03 |
| 16.5 | 6.70 |
| 18.3 | 13.86 |
| 19.0 | 6.68 |
| 20.7 | 10.02 |
| 21.3 | 7.02 |
| 22.8 | 24.68 |
| 24.0 | 100.00 |
| 28.3 | 33.26 |
| 32.7 | 6.35 |
| 36.0 | 3.28 |
| 38.5 | 6.02 |

In some embodiments, the crystalline glycolate salt of has peaks at diffraction angle 2θ (°) of 7.6°±0.5, e.g., 7.6°±0.2, 10.7°±0.5, e.g., 10.7°±0.2, and 24.0°±0.5, e.g., 24.0°±0.2 as measured by X-ray diffractometry by irradiation with Cu Kα X-rays or calculated from X-ray diffractometry. In some embodiments, the most intense peak in the X-ray diffraction diagram is observed at an angle of refraction 2θ of 7.6°±0.5, e.g., 7.6°±0.2. In an essentially pure material of the crystalline glycolate salt of sepiapterin, peaks can be observed at angles of refraction 2θ as set forth in Table 20. Alternatively or in addition, the crystalline glycolate salt of sepiapterin is characterized by a DSC curve showing two endotherms at 133.9° C. and 147.7° C.

TABLE 20

| Position [2θ°] (±0.5, e.g., ±0.2) | Relative Intensity |
|---|---|
| 4.8 | 6.23 |
| 7.6 | 100.00 |
| 10.3 | 68.06 |
| 10.7 | 70.69 |
| 15.3 | 36.51 |
| 18.2 | 24.25 |
| 18.7 | 27.26 |
| 19.9 | 2.66 |
| 21.2 | 17.11 |
| 24.0 | 96.62 |
| 24.4 | 18.44 |
| 28.8 | 47.57 |
| 30.3 | 7.43 |
| 32.5 | 4.42 |
| 33.3 | 7.49 |
| 34.3 | 5.21 |
| 36.3 | 7.37 |

In some embodiments, the crystalline acetate salt of has peaks at diffraction angle 2θ (°) of 6.2°±0.5, e.g., 6.2°±0.2, 12.0°±0.5, e.g., 12.0°±0.2, and 18.1°±0.5, e.g., 18.1°±0.2 as measured by X-ray diffractometry by irradiation with Cu Kα X-rays or calculated from X-ray diffractometry. In some embodiments, the most intense peak in the X-ray diffraction diagram is observed at an angle of refraction 2θ of at least 6.2°±0.5, e.g., 6.2°±0.2. In an essentially pure material of the crystalline acetate salt of sepiapterin, peaks can be observed at angles of refraction 2θ as set forth in Table 21. Alternatively or in addition, the crystalline acetate salt of sepiapterin is characterized by a DSC curve showing two endotherms at 146.1° C. and 175.4° C.

TABLE 21

| Position [2θ°] (±0.5, e.g., ±0.2) | Relative Intensity |
| --- | --- |
| 6.2 | 100.00 |
| 10.2 | 23.29 |
| 12.0 | 71.59 |
| 18.1 | 31.27 |
| 21.1 | 20.29 |
| 24.2 | 14.92 |
| 25.2 | 23.03 |
| 27.3 | 13.30 |
| 29.1 | 12.95 |

In some embodiments, the crystalline Form 1 sulfate salt of sepiapterin has peaks at diffraction angle 2θ (°) of 5.1°±0.5, e.g., 5.1°±0.2, 7.8°±0.5, e.g., 7.8°±0.2, and 23.0°±0.5, e.g., 23.0°±0.2 as measured by X-ray diffractometry by irradiation with Cu Kα X-rays or calculated from X-ray diffractometry. In some embodiments, the most intense peak in the X-ray diffraction diagram is observed at an angle of refraction 2θ of 5.1°±0.5, e.g., 5.1°±0.2. In an essentially pure material of the crystalline Form 1 sulfate salt of sepiapterin, peaks can be observed at angles of refraction 2θ as set forth in Table 22. Alternatively or in addition, the crystalline form 1 sulfate salt of sepiapterin is characterized by a DSC curve showing three endotherms at 94.5° C., 158.3° C., and 209.9° C.

TABLE 22

| Position [2θ°] (±0.5, e.g., ±0.2) | Relative Intensity |
| --- | --- |
| 5.1 | 100.00 |
| 6.8 | 3.33 |
| 7.8 | 43.48 |
| 10.2 | 15.92 |
| 15.7 | 18.13 |
| 17.2 | 8.33 |
| 18.7 | 6.49 |
| 19.8 | 5.19 |
| 21.3 | 5.52 |
| 23.0 | 19.05 |
| 23.5 | 8.29 |
| 24.2 | 5.59 |
| 24.8 | 17.44 |
| 25.7 | 4.97 |
| 26.7 | 10.38 |
| 28.7 | 11.49 |
| 30.4 | 2.88 |
| 31.0 | 3.67 |

In some embodiments, the crystalline Form 2 sulfate salt of sepiapterin has peaks at diffraction angle 2θ (°) of 7.8°±0.5, e.g., 7.8°±0.2, 8.8°±0.5, e.g., 8.8°±0.2, and 24.1°±0.5, e.g., 24.1°±0.2 as measured by X-ray diffractometry by irradiation with Cu Kα X-rays or calculated from X-ray diffractometry. In some embodiments, the most intense peak in the X-ray diffraction diagram is observed at an angle of refraction 2θ of 8.8°±0.5, e.g., 8.8°±0.2. In an essentially pure material of the crystalline Form 2 sulfate salt of sepiapterin, peaks can be observed at angles of refraction 2θ as set forth in Table 23.

TABLE 23

| Position [2θ°] (±0.5, e.g., ±0.2) | Relative Intensity |
| --- | --- |
| 5.0 | 4.71 |
| 7.9 | 72.24 |

TABLE 23-continued

| Position [2θ°] (±0.5, e.g., ±0.2) | Relative Intensity |
| --- | --- |
| 8.8 | 100.00 |
| 14.5 | 19.26 |
| 15.7 | 59.40 |
| 16.1 | 8.69 |
| 17.2 | 14.82 |
| 17.7 | 10.89 |
| 19.3 | 9.92 |
| 20.2 | 9.60 |
| 23.7 | 15.38 |
| 24.2 | 43.88 |
| 25.0 | 11.44 |
| 26.8 | 16.81 |
| 28.7 | 16.07 |
| 29.4 | 13.84 |
| 31.3 | 17.14 |
| 31.7 | 7.26 |
| 35.7 | 5.75 |

The present invention may employ a pharmaceutical composition including a pharmaceutically acceptable excipient and an effective amount of sepiapterin, or a pharmaceutically acceptable salt thereof. Examples of pharmaceutical compositions of sepiapterin and salts thereof can be found in WO 2019/046849 and WO 2019/232120, the compositions of which are incorporated herein by reference in their entirety.

The pharmaceutically acceptable excipient can be any of those conventionally used and is limited only by chemico-physical considerations, such as solubility and by the route of administration. It will be appreciated by one of skill in the art that, in addition to the following described pharmaceutical compositions, sepiapterin can be formulated as inclusion complexes, such as cyclodextrin inclusion complexes, or liposomes.

The pharmaceutically acceptable excipients described herein, for example, vehicles, adjuvants, excipients, or diluents, are well known to those who are skilled in the art and are readily available to the public. It is preferred that the pharmaceutically acceptable excipient be one which is chemically inert to the sepiapterin and one which has no detrimental side effects or toxicity under the conditions of use.

Formulations which Increase Gastric and/or Anterior Intestine Residence Time

Gastro-retentive drug delivery is an approach with the drug formulation is designed to remain in the stomach longer, e.g., until drug release is complete.

Bioadhesive dosage forms utilize polymers that are capable of adhering to surfaces and result in a controlled release of the drug. The bioadhesive polymers may be anionic (e.g., carboxymethylcellulose, alginic acid, polyacrylic acid, pectin, carrageenan, polycarbophil, or carbomer); cationic (e.g., chitosan, polylysine, or polybrene); or non-ionic (e.g., polyethylene glycol, polyvinylpyrrolidone, dextran, or hydroxypropylmethylcellulose).

High-density dosage forms are designed to sit in the stomach at a lower level than the pyloric sphincter, and thus avoid emptying. Excipients suitable for high-density dosage forms include iron powder, barium sulphate, zinc oxide, and titanium oxide.

Expandable dosage forms are designed to expand in the stomach to be larger than the pyloric sphincter, and thus avoid emptying. For example, dosage forms including a drug core, a swellable hydrocolloid, and an outer semipermeable polymer are suitable for expandable dosage forms.

Super-porous hydrogel dosage forms are designed, similarly to expandable dosage forms, to expand in the stomach to be larger than the pyloric sphincter. Super-porous hydrogel dosage forms may include polymers such as crosscarmellose sodium.

Floating dosage forms are designed to have a lower density than gastric fluid. Floating dosage forms may include compositions including ion exchange resin, a raft system, an inflatable chamber, an effervescent mixture, a swellable hydrocolloid, or a multi-particulate system.

Antioxidants

Sepiapterin is prone to rapid oxidation when exposed to air. Accordingly, pharmaceutical compositions of the invention may include antioxidants. The antioxidant may minimize the oxidative degradation of sepiapterin. Examples of antioxidants include, but are not limited to, 4-chloro-2,6-ditert-butylphenol, tocopherol, alpha-tocopherol, alkylated diphenylamines, ascorbic acid, ascorbyl myristate, ascorbyl palmitate, ascorbyl stearate, beta-carotene, butylated hydroxyanisole, butylated hydroxytoluene, citric acid, cysteine, D-alpha-tocopheryl polyethylene glycol 1000 succinate, deferoxamine methanesulfonate, dodecyl gallate, ethylenediaminetetraacetic acid, ethylparaben, folic acid, fumaric acid, gallic acid, glutathione, lecithin, malic acid, methylparaben, monothioglycerol, N-acetyl cysteine, nordihydroguaiaretic acid, octyl gallate, p-phenylenediamine, potassium ascorbate, potassium metabisulfite, potassium sorbate, propionic acid, propyl gallate, retinol, sorbic acid, sodium ascorbate, sodium bisulfite, sodium hydrosulfite, sodium isoascorbate, sodium metabisulfite, sodium sulfite, sodium thiosulfate, tartaric acid, tert-butylhydroquinone, thiourea, tocopheryl acetate, vitamin A, vitamin B6, vitamin B12, or vitamin E. Examples of antioxidants include, but are not limited to, ascorbic acid, tocopherol, retinol, ascorbyl palmitate, N-acetyl cysteine, glutathione, ethylenediaminetetraacetic acid, sodium bisulfite, sodium metabisulfite, thiourea, butylatedhydroxytoluene, butylatedhydroxyanisole, and vitamin E. In some embodiments, the pharmaceutical compositions of the invention include ascorbic acid, tocopherol, retinol, ascorbyl palmitate, N-acetyl cysteine, glutathione, butylatedhydroxytoluene, and/or butylatedhydroxyanisole as antioxidant.

In some embodiments, the pharmaceutical composition includes less than 10% antioxidant by weight, e.g., less than 9%, less than 8%, less than 7%, less than 6%, less than 5%, less than 4%, less than 3%, less than 2%, less than 1%, or substantially free of antioxidant. In some embodiments, the pharmaceutical composition includes 2-9% antioxidant by total weight, e.g., 2-4%, 3-5%, 4-6%, 5-7%, 6-8%, or 7-9%. In some embodiments, the pharmaceutical composition comprises 5-100% of the USP maximum daily dose of the antioxidant, e.g., in some embodiments, the pharmaceutical composition comprises about 5%, 10%, 15%, 20%, 30%, 40%, 50%, 60%, 70%, 80%, 90%, or 100% of the USP maximum daily dose of the antioxidant. In some embodiments, the ratio of sepiapterin to antioxidant is at least 1:1, e.g., 2:1, 3:1, 4:1, 5:1, 6:1, 7:1, 8:1, 9:1, or 10:1 by weight.

Dispersants

In some embodiments, the pharmaceutical compositions of the invention include at least one dispersant. The dispersant may cause particles in the formulation to separate, e.g., release their medicinal substances on contact with moisture. Examples of dispersants include, but are not limited to, crosslinked polyvinylpyrrolidone, carboxymethylcellulose (e.g., croscarmellose salt, e.g., croscarmellose sodium), starch (e.g., sodium starch glycolate), or alginic acid. In some embodiments, the dispersant in the pharmaceutical composition is a carboxymethylcellulose such as a pharmaceutically acceptable salt of croscarmellose. In some embodiments, the pharmaceutical composition may include 0.1-1.5% dispersant by total weight, e.g., about 0.1%, 0.5%, 1%, or 1.5%. In some embodiments, the pharmaceutical composition includes less than 1.5% dispersant, e.g., less than 1%, less than 0.5%, or less than 0.1% by total weight.

Anti-Caking Agents

In some embodiments, the pharmaceutical compositions of the invention include at least one anti-caking agent. In some embodiments, the pharmaceutical compositions include at least two anti-caking agents. Exemplary anti-caking agents include colloidal silicon dioxide, microcrystalline cellulose, tricalcium phosphate, microcrystalline cellulose, magnesium stearate, sodium bicarbonate, sodium ferrocyanide, potassium ferrocyanide, calcium ferrocyanide, calcium phosphate, sodium silicate, colloidal silicon dioxide, calcium silicate, magnesium trisilicate, talcum powder, sodium aluminosilicate, potassium aluminum silicate, calcium aluminosilicate, bentonite, aluminum silicate, stearic acid, and polydimethylsiloxane. In some embodiments, the at least one anti-caking agent is colloidal silicon dioxide or microcrystalline cellulose. In some embodiments, the pharmaceutical composition may include 65-75% anti-caking agent by total weight, e.g., about 65%, 67%, 70%, 73%, or 75%. In some embodiments, the pharmaceutical composition includes both colloidal silicon dioxide and microcrystalline cellulose. In some embodiments, the pharmaceutical composition includes 60-65% microcrystalline cellulose by total weight and 5-7% colloidal silicon dioxide by total weight.

Dosing Vehicle

In some embodiments, the pharmaceutical compositions of the invention are combined with a dosing vehicle prior to administration, e.g., a dosing vehicle with a viscosity of approximately 50-1750 centipoise (cP). One type of suspending agent that can be used is a combination of glycerin and sucrose in water (e.g., MEDISCA® oral mix with 2.5% glycerin and 27% sucrose in water). An appropriate quantity of composition can be added to the dosing vehicle mixture and agitated to suspend the composition just prior to administration.

Other suspending agents may also be used as a dosing vehicle. Exemplary suspending agents include water, agar, alginic acid, sodium carboxymethyl cellulose, carrageenan, dextrin, gelatin, guar gum, hydroxyethyl cellulose, hydroxypropyl cellulose, hypromellose, methyl cellulose, polyethylene glycol, povidone, tragacanth, xanthan gum, or other suspending agents known in the art.

Dosage

Sepiapterin, or pharmaceutically acceptable salt thereof, can be used in any suitable dose. Suitable doses and dosage regimens can be determined by conventional range finding techniques. Generally treatment is initiated with smaller dosages, which are less than the optimum dose. Thereafter, the dosage is increased by small increments until optimum effect under the circumstances is reached. For convenience, the total daily dosage may be divided and administered in portions during the day if desired. In proper doses and with suitable administration of certain compounds, the present invention provides for a wide range of responses. Typically, the dosages range from about 1 to about 150 mg/kg, or about 2.5 to about 150 mg/kg body weight of the subject being treated/day, e.g., 60 mg/kg/day. For example, in embodiments, sepiapterin, or pharmaceutically acceptable salt thereof, may be administered from about 10 mg/kg to about 150 mg/kg, from about 20 mg/kg to about 150 mg/kg, from about 10 mg/kg to about 60 mg/kg, from about 20 mg/kg to about 60 mg/kg, from about 40 mg/kg to about 100 mg/kg, from about 100 mg/kg to about 150 mg/kg, from about 60 mg/kg to about 120 mg/kg, from about 80 mg/kg to about 100 mg/kg, from about 40 mg/kg to about 60 mg/kg, from about 2.5 mg/kg to about 20 mg/kg, from about 2.5 mg/kg to about 10 mg/kg, or from about 2.5 mg/kg to about 5 mg/kg, of subject body weight per day, one or more times a day, to obtain the desired therapeutic effect.

In some embodiments, the sepiapterin, or pharmaceutically acceptable salt thereof, can be formulated into unit solid oral dosage forms such as particles. In these embodiments, each unit solid oral dosage form, e.g., sachet, can comprise any suitable amount of the sepiapterin, or pharmaceutically acceptable salt thereof. For example, each solid oral dosage form can comprise about 2.5 mg, about 5 mg, about 10 mg, about 20 mg, about 30 mg, about 40 mg, about 50 mg, about 60 mg, about 70 mg, about 80 mg, about 90 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 750 mg, about 1 g, about 1.25 g, or about 1.5 g.

Sepiapterin, or a pharmaceutically acceptable salt thereof, can be used in the preparation of liquid formulations, such as in the form of a solution, suspension, or emulsion. Formulations suitable for oral administration include, but are not limited to, (a) capsules, sachets, tablets, lozenges, and troches, each containing a predetermined amount of the active ingredient, as solids or granules; (b) powders; (c) liquid solutions, such as an effective amount of the compound dissolved in diluents, such as water, saline, or orange juice; (d) suspensions in an appropriate liquid; and (e) suitable emulsions. Preferred are solid oral dosage forms such as capsule forms, tablet forms, and powder forms. Capsule forms can be of the ordinary hard- or soft-shelled gelatin type containing, for example, surfactants, lubricants, and inert fillers, such as lactose, sucrose, calcium phosphate, and cornstarch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

Formulations suitable for oral and/or parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compound can be administered in a physiologically acceptable diluent in a pharmaceutical excipient, such as a sterile liquid or mixture of liquids, including water, saline, aqueous dextrose and related sugar solutions, an alcohol, such as ethanol, benzyl alcohol, or hexadecyl alcohol, glycols, such as propylene glycol or polyethylene glycol and other polyethylene alcohols, glycerol ketals, such as 2,2-dimethyl-1,3-dioxolane-4-methanol, ethers, such as poly(ethylene glycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

The present invention features pharmaceutical compositions in an orally tolerable formula that contains a therapeutically effective amount of sepiapterin and less than 10% antioxidant. In some embodiments, the pharmaceutical composition is a granular formulation that is dispersed in a pharmaceutically acceptable excipient, for example the composition can be mixed into water and ingested by a subject (e.g., over the course of 5 to 10 minutes). Suitable formulations for use in the present invention are found in Remington's Pharmaceutical Sciences, Mack Publishing Company, Philadelphia, PA 22nd ed., 2010. Except insofar as any conventional excipient is incompatible with the active ingredient, its use in the pharmaceutical compositions is contemplated. Moreover, for animal (e.g., human) administration, it will be understood that preparations should meet sterility, pyrogenicity, general safety and purity standards as required by FDA Office of Biological Standards.

Solid Dosage Form for Oral Administration

Formulations for oral use include particles containing the active ingredient(s) in a mixture with non-toxic pharmaceutically acceptable excipients, and such formulations are known to the skilled artisan (e.g., U.S. Pat. Nos. 5,817,307, 5,824,300, 5,830,456, 5,846,526, 5,882,640, 5,910,304, 6,036,949, 6,036,949, 6,372,218, hereby incorporated by reference). Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, anti-adhesives (e.g., magnesium stearate, zinc stearate, stearic acid, silicas, hydrogenated vegetable oils, or talc), and anti-caking agents (e.g., colloidal silicon dioxide, microcrystalline cellulose, tricalcium phosphate, microcrystalline cellulose, magnesium stearate, sodium bicarbonate, sodium ferrocyanide, potassium ferrocyanide, calcium ferrocyanide, calcium phosphate, sodium silicate, colloidal silicon dioxide, calcium silicate, magnesium trisilicate, talcum powder, sodium aluminosilicate, potassium aluminum silicate, calcium aluminosilicate, bentonite, aluminum silicate, stearic acid, polydimethylsiloxane). Other pharmaceutically acceptable excipients can be colorants, flavoring agents, plasticizers, humectants, and buffering agents. In some embodiments, excipients (e.g., flavoring agents) are packaged with the composition. In some embodiments, excipients (e.g., flavorings) are packaged separately from the composition (e.g., are combined with the composition prior to administration).

The solid compositions of the invention may include a coating adapted to protect the composition from unwanted chemical changes, (e.g., chemical degradation prior to the release of the active substances). The coating may be applied on the solid dosage form in a similar manner as that described in *Encyclopedia of Pharmaceutical Technology*, supra.

Powders and granulates may be prepared using the ingredients mentioned above in a conventional manner using, e.g., a mixer, a fluid bed apparatus, melt congeal apparatus, rotor granulator, extrusion/spheronizer, or spray drying equipment.

Methods of Treatment

Sepiapterin, or a pharmaceutically acceptable salt thereof, serves as a useful therapeutic for SARS-CoV-2 infection. In particular, sepiapterin, or a pharmaceutically acceptable salt thereof, may be useful in preventing, delaying or mitigating acute respiratory distress in an infected subject. In addition, sepiapterin, or a pharmaceutically acceptable salt thereof, may be useful in preventing or mitigating sepsis in an infected subject. In some embodiments, the infection is a symptomatic infection. In some embodiments, the infection is an asymptomatic infection. In some embodiments, the sepiapterin is administered to the subject prior to showing acute respiratory distress. In some embodiments, the sepiapterin is administered to the subject after showing acute respiratory distress. Thus, the various forms of sepiapterin, or a pharmaceutically acceptable salt thereof, in accordance with the present invention can be administered to a subject in an effective amount to obtain a treatment or amelioration of the disease, disorder or condition.

In some embodiments, the subject is a child (e.g., the subject is less than 18 years old, less than 17 years old, less than 16 years old, less than 15 years old, less than 14 years old, less than 13 years old, less than 12 years old, less than 11 years old, less than 10 years old, less than 9 years old, less than 8 years old, less than 7 years old, less than 6 years old, less than 5 years old, less than 4 years old, less than 3 years old, less than 2 years old, less than 1 year old). In some embodiments, the subject is an adult (e.g., the subject is greater than 18 years old). In some embodiments, the subject is at least 20 years old, at least 20 years old, at least 30 years old, at least 40 years old, at least 50 years old, at least 60 years old, at least 70 years old, at least 80 years old.

Sepiapterin, or a pharmaceutically acceptable salt thereof, may or may not be administered with food. Without being bound by theory, administration of sepiapterin with food results in an increase in plasma exposure of BH4, e.g., by reducing the rate of absorption of sepiapterin. If the administered sepiapterin is absorbed quickly, e.g., by being administered on an empty stomach, sepiapterin reductase and/or dihydrofolate reductase in the cells may become saturated above $V_{max}$ resulting in at least a portion of the administered sepiapterin leaving the cell without being reduced to 7,8-dihydrobiopterin and subsequently to BH4. This excess sepiapterin may then be excreted without ever being converted to BH4, resulting in lower levels of BH4 in the plasma compared to administration of sepiapterin with food which reduces the rate of or prolongs the absorption of sepiapterin and results in reaction rates below, at or slightly above the $V_{max}$ for substrate saturation of sepiapterin reductase enzyme and/or dihydrofolate reductase. Administration of sepiapterin, or a pharmaceutically acceptable salt thereof, with food unexpectedly results in an increase in the maximum BH4 plasma concentration (Cmax) and the extent of exposure as measured by the area under the concentration time curve of time zero to last concentration ($AUC_{0-last}$) of BH4 compared to administration without food. For example, the effective amount of sepiapterin, or a pharmaceutically acceptable salt thereof, is an amount (e.g., 1 mg/kg to 100 mg/kg per dose, or 2.5 mg/kg to 100 mg/kg) sufficient to produce a BH4 concentration of at least 50 ng/mL (e.g., at least 60 ng/mL, at least 100 ng/mL, at least 200 ng/mL, at least 400 ng/mL, at least 600 ng/mL, at least 1000 ng/mL, or at least 2000 ng/mL, or from 50 ng/mL to 100 ng/mL, from 60 ng/mL to 400 ng/mL, from 200 ng/mL to 600 ng/mL, from 400 ng/mL to 1000 ng/mL, or from 600 ng/mL to 1500 ng/mL) in the plasma of the subject within 10 hours of administration with food. The effective amount may include a dose that is at least 5% (at least 10%, at least 20%, at least 50%, at least 70%, at least 90%, at least 100%, at least 110%, at least 120%, at least 130%, at least 140%, or at least 150%) lower than the dose sufficient to produce a maximum BH4 plasma concentration (Cmax) of at least 50 ng/mL (e.g., at least 60 ng/mL, at least 100 ng/mL, at least 200 ng/mL, at least 400 ng/mL, at least 600 ng/mL, at least 1000 ng/mL, or at least 2000 ng/mL, or from 50 ng/mL to 100 ng/mL from 60 ng/mL to 400 ng/mL, from 200 ng/mL to 600 ng/mL, from 400 ng/mL to 1000 ng/mL, or from 600 ng/mL to 1500 ng/mL) in the plasma of the subject within 10 hours of administration of sepiapterin, or a pharmaceutically acceptable salt thereof, without food.

In some embodiments of any of the methods described herein, the food is a high protein food. In some embodiments of any of the methods described herein, the food is a high fat food (e.g., at least 25, 30, 40, or 50% of the calories are from fat). In some embodiments of any of the methods described herein, the food is a high protein and high fat food. In some embodiments, the food is high calorie food (e.g., the food includes at least 100 calories, e.g., at least 200 calories, at least 300 calories, at least 400 calories, at least 500 calories, e.g., 500-1500 or 800-1000 calories). In some embodiments of any of the methods described herein, the food is a meal, e.g., breakfast, lunch, or dinner. The sepiapterin, or a pharmaceutically acceptable salt thereof, may be provided in a separate composition from the consumed food (e.g., the sepiapterin, or a pharmaceutically acceptable salt thereof, is not incorporated into a food product). In some embodiments of any of the methods described herein, the food is a low fat food.

Administration to the subject may occur less than 30 minutes prior to consuming food or after consuming food, e.g., immediately prior to the consumption of food up to 1 hour after consumption, such as substantially at the same time as food. The administration with food (e.g., occurring less than 30 minutes prior to consuming food or after consuming food, e.g., immediately prior to the consumption of food up to 1 hour after consumption) may result in an increase (e.g., at least 5%, at least 10%, at least 20%, at least 30%, at least 40%, at least 50%, at least 60%, at least 70%, at least 80%, at least 90%, at least 100%, at least 110%, at least 120%, at least 130%, at least 140%, or at least 150%) in the Cmax of BH4 or in the extent of production and resulting plasma exposure ($AUC_{0-last}$) of BH4 compared to administration without food (e.g., occurring more than 2 hours after consuming food until 30 minutes prior to consuming further food).

The sepiapterin or pharmaceutically acceptable salt thereof, may be administered to the subject without food, for example, more than 30 minutes prior to consuming food, or at least 2 hours after consuming food. In some embodiments in any of the methods described herein, administration occurs more than 30 minutes prior to consuming food, or at least 3 hours after consuming food. In some embodiments of any of the foregoing methods, the sepiapterin or salt pharmaceutically acceptable salt thereof, is administered without a high protein food. In some embodiments of any of the foregoing methods, the sepiapterin, or pharmaceutically acceptable salt thereof, is administered without a high fat food (e.g., at least 25, 30, 40, or 50% of the calories are from fat). In some embodiments of any of the foregoing methods the sepiapterin, or pharmaceutically acceptable salt thereof, is administered without a high protein and high fat food. In some embodiments, the sepiapterin, or pharmaceutically acceptable salt thereof, is administered without a high calorie food (e.g., the food includes at least 100 calories, e.g., at least 200 calories, at least 300 calories, at least 400 calories, at least 500 calories, e.g., 500-1500 or 800-1000 calories). In some embodiments of any of the foregoing methods, the sepiapterin, or pharmaceutically acceptable salt thereof, is administered without the food being a meal, e.g., breakfast, lunch, or dinner.

Without being bound by theory, administration of sepiapterin, or pharmaceutically acceptable salt thereof, without food may result in an increase in plasma, CSF, and/or brain exposure of sepiapterin by increasing the rate of absorption of sepiapterin. As sepiapterin passes through cell membranes efficiently, if the administered sepiapterin is absorbed quickly, e.g., by being administered on an empty stomach, the active transporters of sepiapterin and/or sepiapterin reductase enzymes in cells may be saturated resulting in at least a portion of the administered sepiapterin not entering the cells and/or leaving the cell without being reduced to 7,8-dihydrobiopterin. This excess sepiapterin in the plasma may then cross the blood brain barrier (BBB) and enter into brain cells prior to being converted to BH4, resulting in higher levels of BH4 in the brain (and/or CSF) compared to administration with food, which reduces the rate of absorption of sepiapterin and may not result in saturation of the sepiapterin transporters and intracellular sepiapterin reductase enzymes. Thus, administration of sepiapterin, or pharmaceutically acceptable salt thereof, without food unexpectedly results in an increase in the maximum plasma, CSF, and/or brain concentration (Cmax) and/or the extent of absorption ($AUC_{0\text{-}last}$) of sepiapterin compared to administration with food. The increased levels of sepiapterin in the plasma, CSF, and/or brain may be beneficial during treatment.

The actual dosage amount of a composition of the present invention administered to a subject can be determined by physical and physiological factors such as body weight, severity of condition, the type of disease being treated, previous or concurrent therapeutic interventions, idiopathy of the subject and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In some embodiments, subjects receive about 1 mg/kg to 120 mg/kg per dose (e.g., about 10 mg/kg to about 60 mg/kg, about 20 mg/kg to about 60 mg/kg, or about 10 mg/kg, or about 20 mg/kg, about 30 mg/kg, about 40 mg/kg, about 50 mg/kg, about 60 mg/kg). Subjects may receive the pharmaceutical composition including sepiapterin, or a pharmaceutically acceptable salt thereof, once daily, twice daily or three times daily during treatment. In some embodiments, subjects may not be permitted to take any drugs known to inhibit folate synthesis (e.g., methotrexate, pemetrexed, or trimetrexate). Sepiapterin, or a pharmaceutically acceptable salt thereof, may be administered in two equal doses (e.g., two doses at different times of day), e.g., two 60 mg/kg doses (e.g., one 60 mg/kg dose in the morning and one 60 mg/kg dose in the evening), two 40 mg/kg doses (e.g., one 40 mg/kg dose in the morning and one 40 mg/kg dose in the evening), two 30 mg/kg doses (e.g., one 30 mg/kg dose in the morning and one 30 mg/kg dose in the evening), two 20 mg/kg doses (e.g., one 20 mg/kg dose in the morning and one 20 mg/kg dose in the evening), or two 10 mg/kg doses (e.g., one 10 mg/kg dose in the morning and one 10 mg/kg dose in the evening).

EQUIVALENTS AND SCOPE

Those skilled in the art will recognize or be able to ascertain using no more than routine experimentation, many equivalents to the specific embodiments in accordance with the invention described herein. The scope of the present invention is not intended to be limited to the above Description, but rather is as set forth in the appended claims.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any compound; any method of production; any method of use; etc.) can be excluded from any one or more claims, for any reason, whether or not related to the existence of prior art.

1. Guan, W. et al. Clinical Characteristics of Coronavirus Disease 2019 in China. N. Engl. J. Med. (2020). doi:10.1056/nejmoa2002032
2. Xu, Z. et al. Pathological findings of COVID-19 associated with acute respiratory distress syndrome. Lancet Respir. Med. (2020). doi:10.1016/S2213-2600 (20)30076-X
3. Shi, Y. et al. COVID-19 infection: the perspectives on immune responses. Cell Death Differ. (2020). doi: 10.1038/s41418-020-0530-3
4. Cardnell, R. J. G. Rabender C S, Ross G R, Guo C, Howlett E L, Alam A, Wang X Y, Akbarali H I, Mikkelsen R B. Sepiapterin ameliorates chemically induced murine colitis and azoxymethane-induced colon cancer. J. Pharmacol. Exp. Ther. (2013). doi: 10.1124/jpet.113.203828
5. Cronin, S. J. F. et al. The metabolite BH4 controls T cell proliferation in autoimmunity and cancer. Nature (2018). doi:10.1038/s41586-018-0701-2
6. Bentzen, S. M. Preventing or reducing late side effects of radiation therapy: Radiobiology meets molecular pathology. Nature Reviews Cancer (2006). doi: 10.1038/nrc1950
7. Cai, S., Khoo, J. & Channon, K. M. Augmented BH4 by gene transfer restores nitric oxide synthase function in hyperglycemic human endothelial cells. Cardiovasc. Res. (2005). doi:10.1016/j.cardiores.2004.10.040
8. Wever, R. M. F., Van Dam, T., Van Rijn, H. J. M., De Groot, F. & Rabelink, T. J. Tetrahydrobiopterin regulates superoxide and nitric oxide generation by recombinant endothelial nitric oxide synthase. Biochem. Biophys. Res. Commun. (1997). doi:10.1006/bbrc.1997.7069
9. Schmidt, H. H. H. W. et al. No NO from NO synthase. Proc. Natl. Acad. Sci. U.S.A (1996). doi:10.1073/pnas.93.25.14492

10. Rabender, C. S. Alam A, Sundaresan G, Cardnell R J, Yakovlev V A, Mukhopadhyay N D, Graves P, Zweit J, Mikkelsen R B. The role of nitric oxide synthase uncoupling in tumor progression. Mol. Cancer Res. (2015). doi:10.1158/1541-7786.MCR-15-0057-T 11. Rabender C S, Bruno N, Alam A, Sundaresan G, Cardnell R J, Yakovlev V A, Mukhopadhyay N D, Graves P, Zweit J, Mikkelsen R B. Sepiapterin enhances tumor radio- and chemosensitivities by vascular normalization. J Pharmacol Exp Ther. 2018 June; 365(3):536-543. doi: 10.1124/jpet.117.245258.

12. Vásquez-Vivar, J. et al. Superoxide generation by endothelial nitric oxide synthase: The influence of cofactors. Proc. Natl. Acad. Sci. U.S.A (1998). doi: 10.1073/pnas.95.16.9220

13. Vśquez-Vivar, J., Kalyanaraman, B. & Martasek, P. The role of tetrahydrobiopterin in superoxide generation from eNOS: Enzymology and physiological implications. Free Radical Research (2003). doi:10.1080/1071576021000040655

14. Stuehr, D., Pou, S. & Rosen, G. M. Oxygen Reduction by Nitric-oxide Synthases. Journal of Biological Chemistry (2001). doi:10.1074/jbc.R100011200

15. Mikkelsen, R. B. & Wardman, P. Biological chemistry of reactive oxygen and nitrogen and radiation-induced signal transduction mechanisms. Oncogene (2003). doi:10.1038/sj.onc.1206663

16. Alp, N. J. & Channon, K. M. Regulation of Endothelial Nitric Oxide Synthase by Tetrahydrobiopterin in Vascular Disease. Arteriosclerosis, Thrombosis, and Vascular Biology (2004). doi:10.1161/01.ATV.0000110785.96039.f6

17. Kelleher, Z. T., Matsumoto, A., Stamler, J. S. & Marshall, H. E. NOS2 regulation of NF-κB by S-nitrosylation of p65. J. Biol. Chem. (2007). doi:10.1074/jbc.M705929200

18. Marshall, H. E. & Stamler, J. S. Inhibition of NF-κB by S-nitrosylation. Biochemistry (2001). doi:10.1021/bi002239y 19. Yakovlev V A, Barani I J, Rabender C S, Black S M, Leach J K, Graves P R, Kellogg G E, Mikkelsen R B Tyrosine Nitration of Ik-Balpha: a novel mechanism of NF-kBalpha activation. Biochemistry (2007) doi: 10.1021/bi701107z.

20. Lu, T. et al. Tumor-infiltrating myeloid cells induce tumor cell resistance to cytotoxic T cells in mice. J. Clin. Invest. (2011). doi:10.1172/JCI45862

21. Lu, T. & Gabrilovich, D. I. Molecular pathways: Tumor-infiltrating myeloid cells and reactive oxygen species in regulation of tumor microenvironment. Clin. Cancer Res. (2012). doi:10.1158/1078-0432.CCR-11-2939

22. Nagaraj, S. et al. Altered recognition of antigen is a mechanism of CD8+ T cell tolerance in cancer. Nat. Med. (2007). doi:10.1038/nm1609

23. Molon, B. et al. Chemokine nitration prevents intratumoral infiltration of antigen-specific T cells. J. Exp. Med. (2011). doi:10.1084/jem.20101956

24. Sato, E., Simpson, K. L., Grisham, M. B., Koyama, S. & Robbins, R. A. Effects of reactive oxygen and nitrogen metabolites on RANTES- and IL-5-induced eosinophil chemotactic activity in vitro. Am. J. Pathol. (1999). doi:10.1016/S0002-9440(10)65154-1

25. Sato, E., Simpson, K. L., Grisham, M. B., Koyama, S. & Robbins, R. A. Effects of reactive oxygen and nitrogen metabolites on MCP-1-induced monocyte chemotactic activity in vitro. Am. J. Physiol.-Lung Cell. Mol. Physiol. (1999). doi:10.1152/ajplung.1999.277.3.1543

26. Smith N, Longo N, Levert K, Hyland K, Blau N. Phase I clinical evaluation of CNSA-001 (sepiapterin), a novel pharmacological treatment for phenylketonuria and tetrahydrobiopterin deficiencies, in healthy volunteers. Mol Genet Metab. 2019 April; 126(4):406-412. doi: 10.1016/j.ymgme.2019.02.001

EXAMPLES

Example 1

Mice were treated with either 10 mg/kg sepiapterin (SP) per day delivered via oral gavage or nothing for 3 days. Mice were then treated with 40 ug lipopolysaccharide (LPS) inhaled intranasally. 16-18 hours later, bronchoalveolar lavage (BAL) fluid was collected and assess for cytokine expression via ELISA. Untreated (UT) (n=1), LSP (n=3), LSP+SP (n=2). (FIG. 1). As shown in FIG. 1, sepiapterin administration resulted in lower levels of cytokine expression.

Example 2

$1 \times 10^5$ pmel splenocytes were labeled with carboxyfluorescein succinimidyl ester (CFSE) and then co-cultured, at either a 1:10 or 1:40 ratio (splenocytes:BMDC), with gp100-pulsed bone marrow derived dendritic cells (BMDCs) for 3 days. Sepiapterin (SP) was added after BMDCs were added to splenocytes. After incubation, CFSE dilution was measured via flow cytometry (FIG. 2A) and cytokine expression was measured via ELISA (FIGS. 2B and 2C). No DC=no dendritic cells, UT=untreated. As shown in FIGS. 2A and 2B/2C, respectively, addition of SP enhanced proliferation of anti-viral CD8$^+$ T cells in a dose dependent manner, without directly affecting T cell activation and IFN-γ secretion. The enhanced secretion of IFN-γ in FIG. 2B is a result of the higher number of T cells present in wells treated with SP.

Example 3

$2 \times 10^6$ OT-I splenocytes were injected into C57/B16 mice via tail vein injection. 24 hours later, $1 \times 10^6$ ova peptide-pulsed bone marrow derived dendritic cells were injected into these mice subcutaneously. Starting on day 3, mice were given 10 mg/kg SP orally for 3 consecutive days. On day 6, mice were sacrificed and spleens were harvested and stimulated for 6 hours with brefeldin A (BFA), phorbol myristate acetate (PMA), and ionomycin. OT-I proliferation (FIG. 3A) and IFN-γ expression (FIG. 3B) were assessed via flow cytometry. As shown in FIGS. 3A-3B, respectively, addition of SP enhanced proliferation of OT-I cells (i.e. enhanced T cell proliferation), with minimal effect on T cell activation and IFN-γ secretion.

Other embodiments are in the claims.

What is claimed is:

1. A method of therapeutic treatment of a SARS-CoV-2 infection in a human subject in need thereof, the method comprising administering to the subject an effective amount of sepiapterin or a pharmaceutically acceptable salt thereof, and wherein the method comprises mitigating acute respiratory distress.

2. The method of claim 1, wherein the infection is a symptomatic infection.

3. The method of claim 1, wherein the sepiapterin, or a pharmaceutically acceptable salt thereof, is administered as soon as the subject demonstrates one or more symptoms of SARS-CoV-2 infection.

4. The method of claim 1, wherein the method comprises mitigating sepsis.

5. The method of claim 1, wherein the effective amount of sepiapterin, or pharmaceutically acceptable salt thereof, is about 10 mg/kg to about 60 mg/kg per dose.

6. The method of claim 1, wherein the effective amount of sepiapterin, or pharmaceutically acceptable salt thereof, is administered once daily.

7. The method of claim 1, wherein the effective amount of sepiapterin, or pharmaceutically acceptable salt thereof, is administered twice daily.

8. The method of claim 7, wherein the effective amount of sepiapterin, or pharmaceutically acceptable salt thereof, is administered in two equal doses.

9. The method of claim 1, wherein the effective amount of sepiapterin, or a pharmaceutically acceptable salt thereof, is administered with food.

10. The method of claim 9, wherein administration to the subject occurs less than 30 minutes prior to consuming food or after consuming food.

11. The method of claim 9, wherein the administration to the subject is substantially at the same time as food.

12. The method of claim 1, wherein the sepiapterin, or a pharmaceutically acceptable salt thereof, is administered as an oral powder in suspension.

13. The method of claim 1, wherein the sepiapterin, or a pharmaceutically acceptable salt thereof, is administered as a suspension in a flavored suspending vehicle.

14. The method of claim 1, wherein the sepiapterin, or a pharmaceutically acceptable salt thereof, is administered as a suspension in water or juice.

15. The method of claim 1, wherein the method comprises mitigating fibrotic disease resulting from acute respiratory distress.

16. The method of claim 1, wherein the effective amount of sepiapterin, or pharmaceutically acceptable salt thereof, is administered for at least 14 days.

17. The method of claim 1, wherein the effective amount of sepiapterin, or pharmaceutically acceptable salt thereof, is administered for 14-30 days.

* * * * *